US007116812B2

(12) United States Patent
Langan et al.

(10) Patent No.: US 7,116,812 B2
(45) Date of Patent: Oct. 3, 2006

(54) METHOD AND APPARATUS FOR PROVIDING A STANDARD VIDEO INTERFACE

(75) Inventors: David Allen Langan, Clifton Park, NY (US); Nick Andrew Van Stralen, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 735 days.

(21) Appl. No.: 10/248,560

(22) Filed: Jan. 29, 2003

(65) Prior Publication Data

US 2004/0146192 A1 Jul. 29, 2004

(51) Int. Cl.
*G06K 9/00* (2006.01)

(52) U.S. Cl. ............................ 382/132; 378/4; 378/92; 710/22

(58) Field of Classification Search ................ 382/128, 382/129, 130–134; 250/370.09, 390.02; 378/4, 37, 46, 62, 90, 92, 101, 140, 901; 710/22, 27, 308; 714/9; 715/716, 719
See application file for complete search history.

(56) References Cited

U.S. PATENT DOCUMENTS

| | | | | | |
|---|---|---|---|---|---|
| 4,259,725 | A | * | 3/1981 | Andrews et al. | ............ 715/856 |
| 4,680,628 | A | * | 7/1987 | Wojcik et al. | ............. 378/98.2 |
| 6,005,911 | A | * | 12/1999 | Cheung | ......................... 378/37 |
| 6,115,757 | A | * | 9/2000 | Honda | ......................... 710/22 |
| 6,143,003 | A | * | 11/2000 | Cosman | ....................... 606/130 |
| 6,154,560 | A | * | 11/2000 | Cothren et al. | ............. 382/128 |

OTHER PUBLICATIONS

Amorphous-silicon Image Sensors, http://www.dpix.com/sensors/sensors.htm, 1 page, (May, 2000), dpiX, LLC, Palo Alto, CA.
PCI Local Bus, Chapter 1, Introduction, pp. 1-5.
Microsoft Computer Dictionary (Fourth Edition) 1999, 6 pages, Microsoft Press, Redmond, Washington.
L.E. Antonuk et al., "Strategies to improve the signal and noise performance of active matrix, flat-panel imagers for diagnostic x-ray application," Med. Phys. 27(2):289-306, (Feb. 2000) Am. Assoc. Phys. Med.
S. L. Garverick et al., "A 32-Channel Charge Readout IC for Programmable, Nonlinear Quantization of Multichannel Detector Data," IEEE Journal of Solid-State Circuits, 30(5):533-541 (May 1995), IEEE.

(Continued)

*Primary Examiner*—Jingge Wu
*Assistant Examiner*—Abolfazi Tabatabai
(74) *Attorney, Agent, or Firm*—Fletcher Yoder

(57) ABSTRACT

An imaging system and method includes a detector framing node (DFN) being programmable to receive image data from a panel detector, and to store the image data for later transfer of the image data by way of a direct memory access (DMA) transfer. The imaging system and method also includes a DFN control unit configured to control operation of the DFN and to output at least one DMA instruction to the DFN, the at least one DMA instruction corresponding to a dummy DMA instruction that disables a start of a DMA transfer corresponding to execution of the at least one DMA instruction. The imaging system and method further includes an auxiliary image interface being programmable to detect the dummy DMA instruction, to issue a DMA request to the DFN in accordance with the dummy DMA instruction, and to convert data received from the DFN into a different format, to output to a host unit that is capable of processing the data received in the different format.

35 Claims, 27 Drawing Sheets

OTHER PUBLICATIONS

McGraw-Hill Encyclopedia of Science & Technology, "Charge-coupled devices," vol. 3, pp. 475-478, BOR-CLE, 7th Edition, McGraw-Hill, Inc., New York.

McGraw-Hill Encyclopedia of Science & Technology, "Computerized tomography," vol. 4, pp. 283-285, CLI-CYT, 7th Edition, McGraw-Hill, Inc., New York.

McGraw-Hill Encyclopedia of Science & Technology, "Medical imaging," vol. 10, pp. 591-594, LEP-MES, 7th Edition, McGraw-Hill, Inc., New York.

McGraw-Hill Encyclopedia of Science & Technology, "Optical Detectors," vol. 12, pp. 416-417, NIO-OZO 7th Edition, McGraw-Hill, Inc., New York.

McGraw-Hill Encyclopedia of Science & Technology, "Photoelasticity," vol. 13, pp. 403, 405, 435-437, PAC-PLAN, 7th Edition, McGraw-Hill, Inc.

McGraw-Hill Encyclopedia of Science & Technology, "Radiography," vol. 15, pp. 136-143, RAB-RYE, 7th Edition, McGraw-Hill, Inc.

McGraw-Hill Encyclopedia of Science & Technology, "X-ray tube," vol. 19, pp. 580-584, ULC-ZYG, 7th Edition, McGraw-Hill, Inc.

E. Hecht, Optics, 3rd Edition, Addison-Wesley Longman, Inc. (1998), pp. 78-79.

A. Paskins, The IEEE 1394 Bus, pp. 4/1-4/6, (1997), The Institution of Electrical Engineers, UK.

An Introduction to the Instrument and Industrial Control Protocol, 6 pages.

C. Severance, "Linking Computers and Consumer Electronics," Standards, Feb. 1997, College of Engineering, pp. 119, 121.

USB—Universal Serial Bus, http://www.lucent.com/micro/usb/usbabout.html, Sep. 2000, 2 pages.

Product Directory—Quality by Design, http://www.tte.thomsom-csf.com:8200/Products_us/Xri/s061_2.jsp., Sep. 2000, 2 pages.

Varian Medical Systems, X-Ray Products (Catalogue), Feb. 2000, 11 pages.

Siemans (Catalogue), "e-soft Workstation" (Sep. 2000), http://www.sms.siemens.com/nmg/ew.html, Sep. 2000, 2 pages.

Thompson (Catalogue) High-definition CCD radiological imaging units, http://www.tte.thomson-csf.com:8200/Products us/Xrt/T017.jsp, Oct. 2000, 3 pages.

* cited by examiner

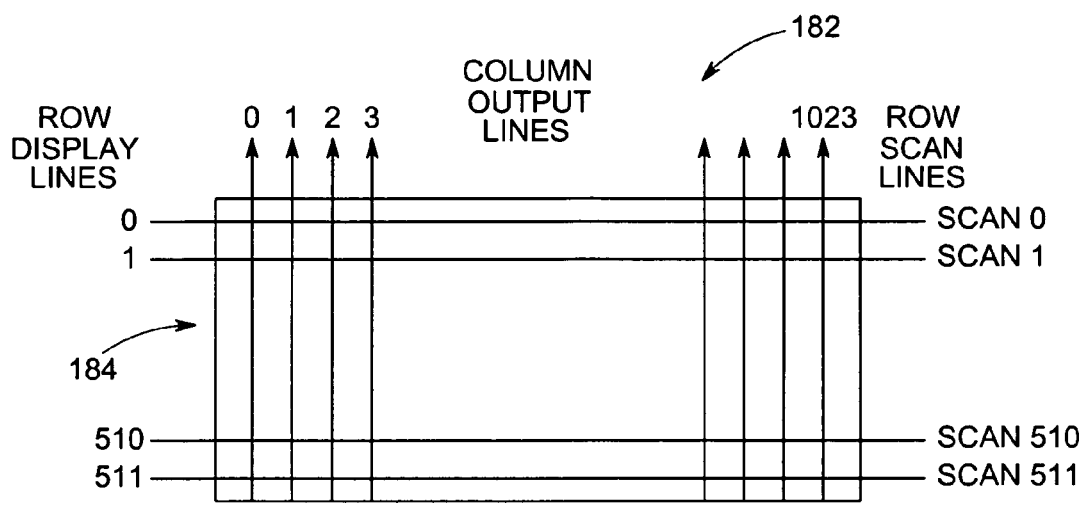
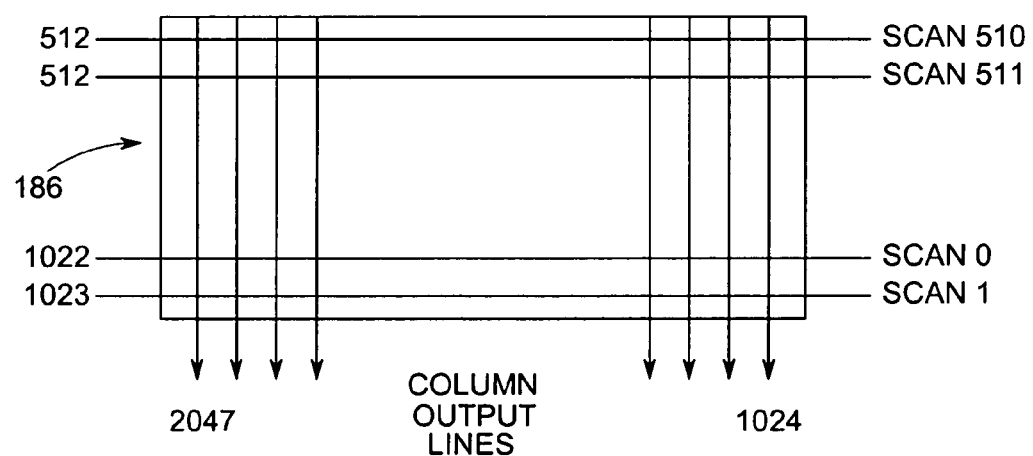
CADIAC/SURGICAL DIGITAL X-RAY PANEL
FIG. 8
(PRIOR ART)

RADIOGRAPHY DIGITAL X-RAY PANEL

FIG. 21

| CAMERA EIA SYSTEM | MODE 1 | | | |
|---|---|---|---|---|
| FRAMES / SEC | 30 | | | |
| LINES / FRAME | 1030 | | | |
| PIXELS / LINE | 1260 | | | |
| ACTIVE HORIZONTAL PIXELS | 1000 | PIXELS | | |
| ACTIVE VERTICAL LINES | 1000 | LINES | | |
| PIXELS CLOCK: | 38.934E+6 | Hz | | |
| PIXELS PERIOD: | 25.684E-9 | S | | |
| HORIZONTAL FREQ: | 30.900E+3 | Hz | | |
| HORIZONTAL PERIOD: | 32.362E-6 | S | 1260 | CLOCKS |
| HORIZONTAL ACTIVE: | 25.684E-6 | S | 1000 | CLOCKS |
| HORIZONTAL BLANKING: | 25.684E-6 | S | 260 | CLOCKS |
| HORIZONTAL FRONT PORCH: | 1.027E-6 | S | 40 | CLOCKS |
| HORIZONTAL SYNC: | 2.517E-6 | S | 98 | CLOCKS |
| HORIZONTAL BANK PORCH: | 3.134E-6 | S | 122 | CLOCKS |
| VERTICAL FREQ: | 30 | Hz | | |
| VERTICAL PERIOD: | 33.333E-3 | S | 1030 | LINES |
| VERTICAL ACTIVE: | 32.362E-3 | S | 1000 | LINES |
| VERTICAL BLANKING: | 970.874E-6 | S | 30 | LINES |
| VERTICAL FRONT PORCH: | 161.812E-6 | S | 5 | LINES |
| VERTICAL SYNC: | 194.175E-6 | S | 6 | LINES |
| VERTICAL BANK PORCH: | 614.887E-6 | S | 19 | LINES |

| CAMERA CCIR SYSTEM | MODE 3 | | | |
|---|---|---|---|---|
| FRAMES / SEC | 25 | | | |
| LINES / FRAME | 1030 | | | |
| PIXELS / LINE | 1320 | | | |
| ACTIVE HORIZONTAL PIXELS | 1000 | PIXELS | | |
| ACTIVE VERTICAL LINES | 1000 | LINES | | |
| PIXELS CLOCK: | 33.990E+6 | Hz | | |
| PIXELS PERIOD: | 29.420E-9 | S | | |
| HORIZONTAL FREQ: | 25.750E+3 | Hz | | |
| HORIZONTAL PERIOD: | 38.835E-6 | S | 1260 | CLOCKS |
| HORIZONTAL ACTIVE: | 29.420E-6 | S | 1000 | CLOCKS |
| HORIZONTAL BLANKING: | 9.415E-6 | S | 260 | CLOCKS |
| HORIZONTAL FRONT PORCH: | 1.177E-6 | S | 40 | CLOCKS |
| HORIZONTAL SYNC: | 2.883E-6 | S | 98 | CLOCKS |
| HORIZONTAL BANK PORCH: | 5.355E-6 | S | 122 | CLOCKS |
| VERTICAL FREQ: | 25 | Hz | | |
| VERTICAL PERIOD: | 40.000E-3 | S | 1030 | LINES |
| VERTICAL ACTIVE: | 38.835E-3 | S | 1000 | LINES |
| VERTICAL BLANKING: | 1.165E-3 | S | 30 | LINES |
| VERTICAL FRONT PORCH: | 194.175E-6 | S | 5 | LINES |
| VERTICAL SYNC: | 233.010E-6 | S | 6 | LINES |
| VERTICAL BANK PORCH: | 737.864E-6 | S | 19 | LINES |
| FRONT PORCH EQU. PLUSE | 2.883E-6 | S | 98 | |
| SERRATION PLUSE | 5.766E-6 | S | 196 | |

METHOD AND APPARATUS FOR PROVIDING A STANDARD VIDEO INTERFACE

BACKGROUND OF THE INVENTION

A. Field of the Invention

The invention relates to a method, system, and apparatus for controlling, acquiring and processing digital radioscopic image data, and in particular to a method, system and apparatus for converting acquired digital radioscopic x-ray image data to a format readable by a mobile C-arm x-ray imaging system that is used to examine a patient's soft tissue and/or bone structure.

B. Description of the Related Art

Medical imaging is a specialty that uses radiation, such as gamma rays, x-rays, high-frequency sound waves, magnetic fields, neutrons, or charged particles to produce images of internal body structures. In diagnostic radiology, radiation is used to detect and diagnose disease, while in interventional radiology, radiation is used to treat disease and bodily abnormalities.

Radiography is the technique of producing an image of any opaque specimen by the penetration of radiation, such as gamma rays, x-rays, neutrons, or charged particles. When a beam of radiation is transmitted through any heterogeneous object, the radiation is differentially absorbed depending upon varying object thickness, density, and chemical composition. The radiation emergent from the object forms a radiographic image, which may then be realized on an image detection medium, such as photographic film directly or by using a phosphor to first create a light image. Radiography is a non-destructive technique of testing a gross internal structure of an object, and is conventionally used in medical and industrial applications. Radiography is used to non-destructively detect medical conditions such as tuberculosis and bone fractures, to diagnose vascular conditions, as well as manufacturing imperfections in materials such as cracks, voids, and porosities.

X-ray radiography finds particular usefulness in medical and industrial applications. X-rays are a form of electromagnetic radiation, and were accidentally discovered in 1895 by Wilhelm Conrad Roentgen. X-rays are alternately referred to as roentgen rays. In circa 1895, Roentgen found that x-rays propagate through an internal object such as a hand and expose photographic film, thereby revealing an internal structure. X-rays exhibit different properties than visible light rays, and were designated by Roentgen as "x-rays," with "x" referring to the unknown. For example, x-rays are not focused with a traditional optical light lens, but rather use sophisticated focusing techniques. Today, x-rays are categorized as electromagnetic radiation having a frequency range extending between 2.4×1016 Hz to 5×1019 Hz. Most x-rays have a wavelength smaller than an atom and therefore interact with matter in a granular fashion, that is, like bullets of photon energy. X-rays are absorbed by materials according to the exponential absorption law $$I_x = I_o e^{-\mu x} = I_o e^{-(\mu/\rho)\rho x} \quad (1.0)$$

where $I_o$ is the initial intensity of the x-ray beam; $I_x$ is the intensity after passage through an object, the object having a thickness x, density $\rho$, linear absorption coefficient $\mu$, and mass absorption coefficient $\mu/\rho$.

X-rays are formed through celestial phenomenon, such as internal reactions of stars and quasars, and through electronic x-ray generation devices, such as x-ray tubes. X-ray tubes generally produce x-rays by accelerating a charged particle, such as an electron, through an electrostatic field and then suddenly stopping the x-ray through collision with a solid target. This collision ionizes the solid target by transporting closely held electrons to a higher energy state. As the electrons in the solid target return to their original energy state, x-rays are produced. X-rays are produced within x-ray tubes by accelerating electrons in a vacuum from a cathode toward an anode, with or without particle beam shaping and accelerating through placement of electrodes.

The electronic detection of x-rays is generally referred to as electronic radiography or radioscopy. Prior to electronic detection, radiographic images were captured on photographic film or displayed on a fluorescent screen. Real time visual observation of x-rays on a fluorescent screen is referred to as fluoroscopy. However, as early as the 1930s photo-multiplier tubes (a form of vacuum tube) were developed to produce an electrical signal in response to received light. Photo-multiplier tubes generally respond well to optical range light rays and are therefore often optically coupled with a scintillating material to detect non-optical electromagnetic radiation. The scintillating material converts non-optical radiation, such as gamma rays (emitted by radioactive isotopes used in nuclear medicine) and x-rays into optical radiation. Beginning circa 1980, photo-multiplier/scintillator detectors are generally being replaced by amorphous silicon based photo-cells.

Radioscopy includes one shot x-ray detection, also known as fluorography, and multiple shot x-ray detection, also known as fluoroscopy. Radio-mammography is a form of radioscopy in which the breast is vigorously compressed prior to exposure to maximize detail and minimize radiation exposure. Computed tomography ("CT"), also called computed axial tomography ("CAT"), is a form of radioscopy in which an x-ray tube is rotated around the body while emitting a narrow x-ray beam. The received x-ray beam information is then combined in a computer to produce a two or three dimensional anatomic medical image. Magnetic resonance imaging ("MRI") is a diagnostic procedure in which a high strength magnet aligns the spin of nuclei within cells of a body, such that each nuclei acts like a radio, both receiving and transmitting radio signals. External radio frequency signals are then applied to the body to disturb the spinning cellular nuclei. After the radio signal is stopped, the nuclei realign with the applied magnetic field while emitting faint radio signals. These faint radio signals correspond to different body tissues and are detected to produce an anatomical image.

Radioscopy and related medical diagnostic imaging technologies use precision control over penetrating radiation and well as precision timing for detection and processing of resultant image data. Medical diagnostic imaging generally acquires and controls a very large amount of image data, which in turn is communicated to computer processing equipment at a very high data rate. To provide control over the generation, detection, and processing of medical diagnostic imaging, computer workstations employ the use of a real time operating system ("RTOS") to control operation.

The GE OEC Series 9800 is a mobile device used to examine a patient's body for any internal injuries to the patient's soft tissue and bones. In its current configuration, at one end of the C-arm there is provided an x-ray generation unit, and at the other end of the C-arm there is provided an x-ray detector. A patient is placed on a cart in an area between the respective ends of the C-arm, and x-rays are passed through portions of the patient's body in order to check for any internal injuries. Each pixel of the x-ray detector used with the GE OEC Series 9800 outputs an x-ray received signal level as an electrical signal to a Charged-Coupled Device (CCD) array, which outputs a respective light signal level. The light signals from the plurality of pixels of the CCD array are focused onto a respective pixel region on a small CCD panel (e.g., 1 inch by 1 inch panel), and that information is provided to a work station. Based on the information received, the work station outputs an image for a user, such as a doctor, to review. Also, based on the image received, the work station can control the amount of x-ray power output by the x-ray generator, and the reception characteristics of the x-ray detector.

The current GE OEC Series 9800 work station receives information from the CCD array in a particular format, with horizontal syncs, vertical syncs, vertical blanks, horizontal blanks, etc. (which is similar to a traditional TV format, or an analog image format such as that used by a monitor for a personal computer). If data is received in any different format, the work station cannot properly process the data.

There is a need to provide an interface that allows x-ray detectors which output x-ray detection signals in a different format to be able to communicate with the GE OEC Series 9800. Also, there is a need to take data in other formats and provide a synchronous stream of digital data in a traditional format with H syncs and V syncs.

SUMMARY OF THE INVENTION

It is therefore desirable to provide an imaging system that includes a converting unit that converts data received in a first format from an x-ray detector into a second format for a host processor, in order for the host processor to be able to process the data. The converting unit includes a detector framing node, which is programmed to receive and store image data from a plurality of different flat panel detectors in a first format. The converting unit also includes an auxiliary image interface, which is coupled to the detector framing node and which is programmed to perform direct memory accesses (DMA) of the data stored in the detector framing node, and to convert the data into a second format for output to a control and display unit. When the auxiliary image interface is decoupled from the detector framing node, the image data in the first format is provided to a host processor that is different from the control and display unit.

According to one aspect of the invention, there is provided an image data acquisition system, which includes a detector framing node (DFN) being programmable to receive image data from a panel detector, and to store the image data into at least one buffer for later transfer of the image data by way of a direct memory access (DMA) transfer. As each buffer is filled with image data, the DFN signals that the buffer is full, by way of a DMA command sent to a communications control interface unit on a local bus of the DFN, whereby the communications control interface unit controls the DMA transfer and outputs the command to an external (PCI) bus to a host processor unit. The DMA command corresponds to a dummy DMA command in which the DMA enable and execute bits are not asserted. The image data acquisition system further includes an auxiliary image interface being programmable to detect the dummy DMA command, to issue a DMA request (with enable and execute bits asserted) in accordance with information obtained from the dummy DMA command, and to convert data received from the buffers into a different format, to output to a host unit that is capable of processing the data received in the different format. When the AIMI is not present in the system, the DFN signals that the buffer is full by way of a DMA command with enable and execute bits asserted, whereby image data is read from the buffers and sent to a memory of the host processor unit by way of the communications control interface managing the DMA transfer and outputting the data to a PCI bus which the host processor unit is communicatively coupled to.

According to another aspect of the invention, there is provided an image data acquisition system, which includes detector framing node (DFN) means for receiving image data from a panel detector, and for storing the image data for later transfer of the image data by way of a direct memory access (DMA) transfer. The system also includes control means for controlling operation of the DFN means and for outputting at least one DMA instruction, the at least one DMA instruction corresponding to a dummy DMA instruction that disables a start of a DMA transfer corresponding to execution of the at least one DMA instruction. The system further includes auxiliary image interface means for detecting the dummy DMA instruction, for issuing a DMA request to the DFN means in accordance with the dummy DMA instruction, and for converting data received from the DFN means into a different format, to output to a host unit that is capable of processing the data received in the different format.

According to yet another aspect of the invention, there is provided an image data acquisition method, which includes receiving image data at a detector framing node as output from a panel detector, and storing the image data for later transfer of the image data by way of a direct memory access (DMA) transfer. The method also includes controlling operation of the DFN and outputting at least one DMA instruction to the DFN, the at least one DMA instruction corresponding to a dummy DMA instruction that disables a start of a DMA transfer corresponding to execution of the at least one DMA instruction. The method further includes detecting, by way of an auxiliary image interface means unit communicatively coupled to the DFN, the dummy DMA instruction, for issuing a DMA request to the DFN in accordance with the dummy DMA instruction. The method still further includes converting data received from the DFN into a different format. The method also includes outputting the converted data to a host unit that is capable of processing the data received in the different format.

BRIEF DESCRIPTION OF THE DRAWINGS

The foregoing advantages and features of the invention will become apparent upon reference to the following detailed description and the accompanying drawings, of which:

FIG. 8 (PRIOR ART) is a schematic diagram of a split panel, cardiac/surgical digital x-ray panel.

FIG. 21 shows a format for a first preferred mode in which data is provided to the OEC 9800 unit, according to at least one embodiment of the invention.

FIG. 22 shows a format for a second preferred mode in which data is provided to the OEC 9800 unit, according to at least one embodiment of the invention.

DETAILED DESCRIPTION OF SPECIFIC EMBODIMENTS

The entire contents of U.S. patent application Ser. No. 09/774,549 (GE Medical System's Docket Number RD-27,937), entitled IMAGING SYSTEM INCLUDING DETECTOR FRAMING NODE, which was filed on Jan. 31, 2001, and which is assigned to the same assignee as this application, are incorporated in their entirety herein by reference. FIGS. 1 through 18 are from the above-mentioned application.

Figure 1:
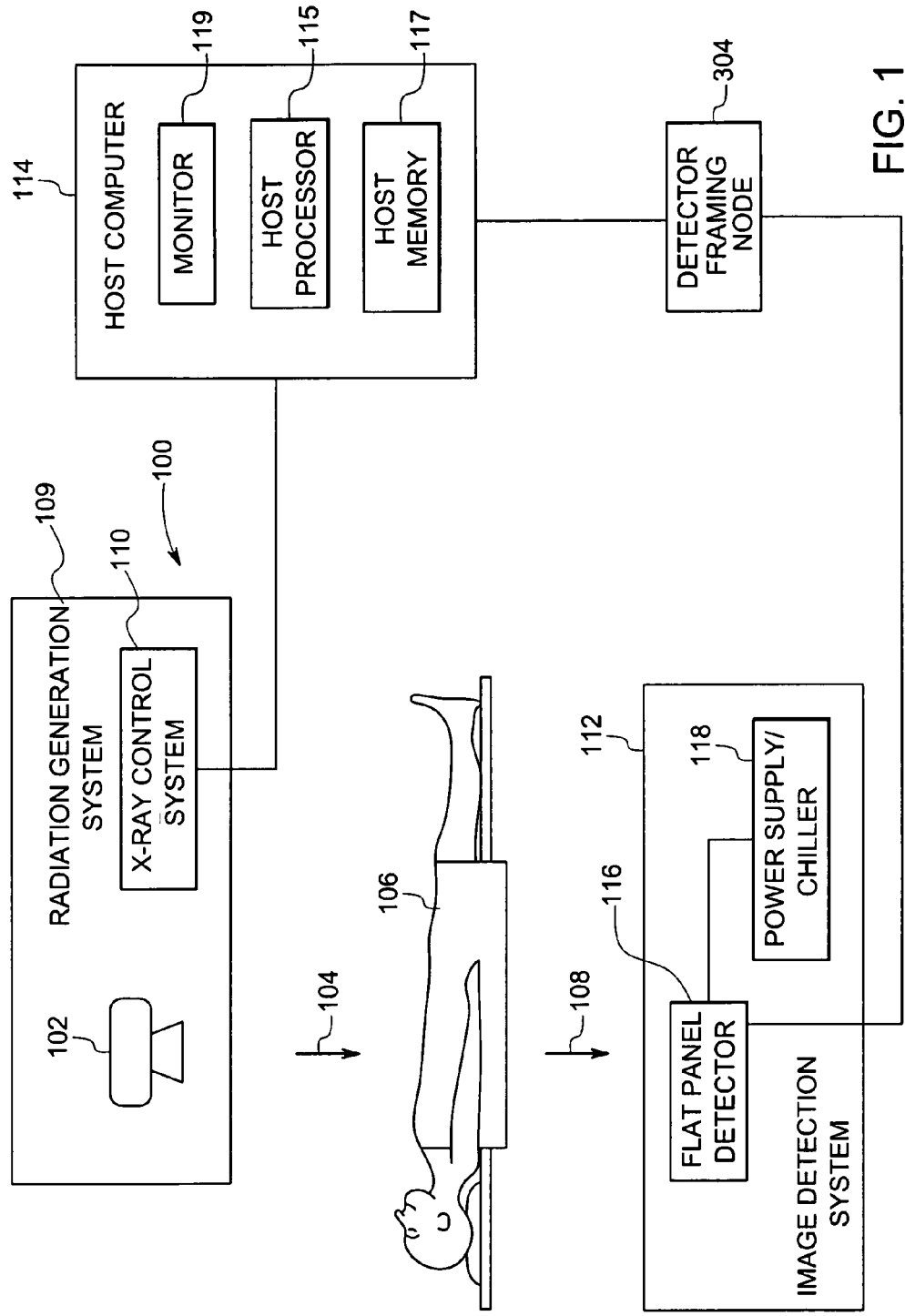
FIG. 1 is a block diagram of an imaging system including a host computer, radiation generation system, and an image detection system.

Referring to FIG. 1, a method, system, and apparatus are illustrated for controlling, acquiring and processing digital radioscopic image data. Imaging system 100 comprises radiation generation system 109, image detection system 112, host computer 114, and detector framing node 304. Host computer 114 includes monitor 119, host processor 115 and host memory 117. According to one construction, imaging system 100 is an image detector monitoring system. According to another construction, the components of imaging system 100 function together as a single apparatus.

Radiation generation system 109 generates radiation to pass through object 106 and to be detected by image detection system 112. According to one construction, radiation generation system 109 includes x-ray generation unit 102 to generate and focus radiation 104 toward object 106. According to one construction, radiation 104 takes the form of x-rays. According to another construction, radiation 104 takes the form of a plurality of sequentially generated radiation bursts. According to one construction, object 106 is in the form of the human body, but it alternatively can be in the form of any other type of animal, mammal, etc. Upon passage through object 106, x-rays 104 form radiographic image 108 for later detection. In general, x-rays are generated by x-ray generation unit 102 in response to control signals output from x-ray control system 110. Radiographic image 108 is received by image detection system 112 and converted into a digital radiographic image. The digital radiographic image is then output from image detection system 112 and transmitted to host computer 114. Host computer 114 provides electronic control to radiation generation system 109 and to image detection system 112.

Image detection system 112 includes flat panel detector 116 for receiving radiographic image 108. Flat panel detector 116 becomes heated during operation, and is therefore connected to power supply/chiller 118 for supplying power and cooling thereto. A digital radiographic image is output from flat panel detector 116 to host computer 114.

Figure 2:
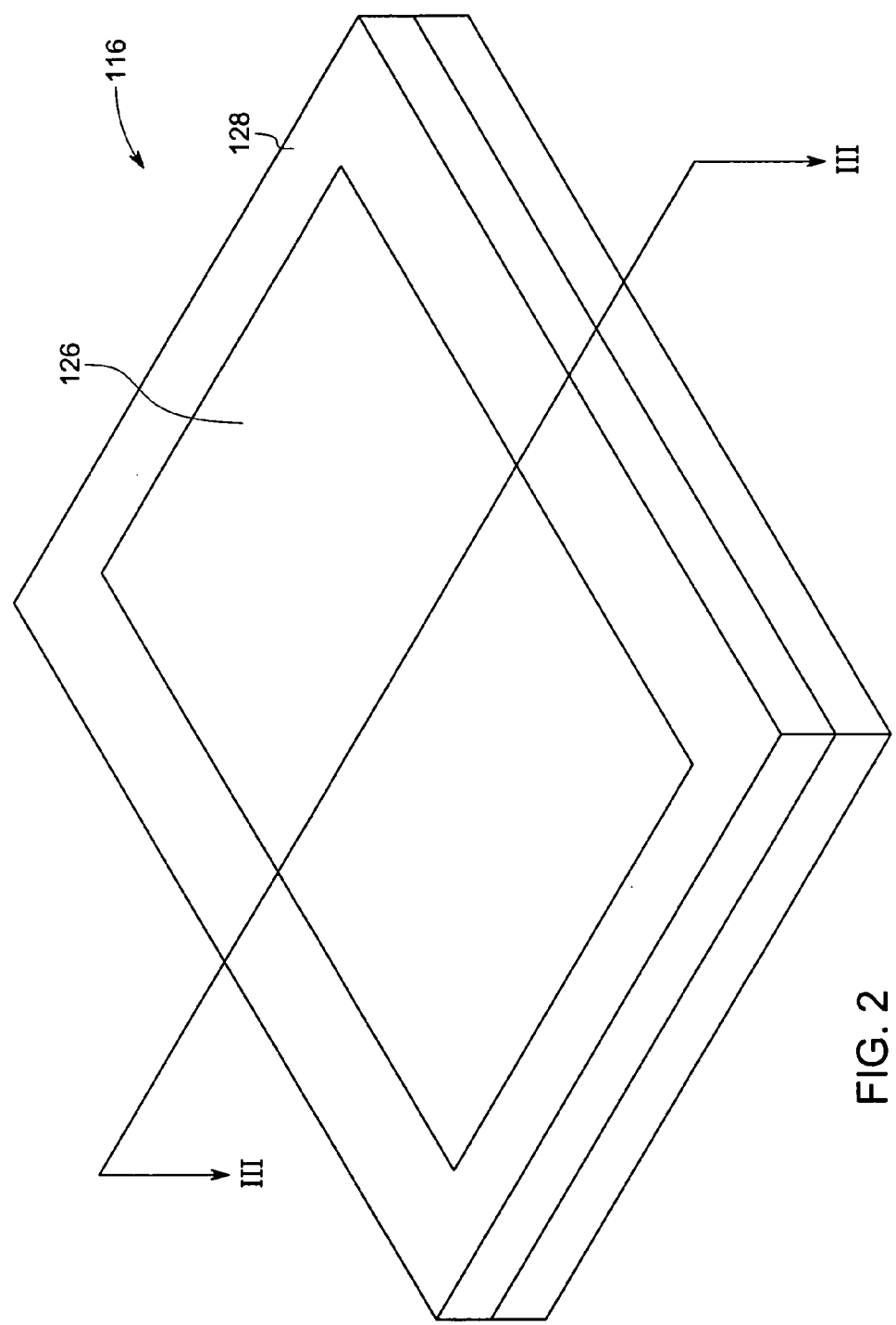
FIG. 2 (PRIOR ART) is an elevated perspective view of a flat panel detector.

FIG. 2 (PRIOR ART) is an elevated perspective view of flat panel detector 116. Flat panel detector 116 is a single detector technology that provides an image receptor in x-ray radiography. For example, flat panel detector 116 replaces existing x-ray imaging films, such as plain film and spot film, for radiographic applications. Moreover, due to thin packaging, flat panel detector 116 replaces imaging intensifiers, video cameras, cine cameras, and photo spot imaging, etc. for digital radiography; and also for digital fluorography and digital fluoroscopy. The area of a flat panel detector 116 is 26 cm×26 cm for a cardiac/surgical digital x-ray panel; 45 cm×56 cm for a radiography digital x-ray panel; and 29 cm×34 cm for a mammography digital x-ray panel. Glass plate 126 and metal casing 128 surround and protect the physical x-ray receptors, electronic detection equipment and associated electronics. In a preferred configuration, flat panel detector is an Apollo detector, manufactured by GE Medical Systems.

Figure 3:
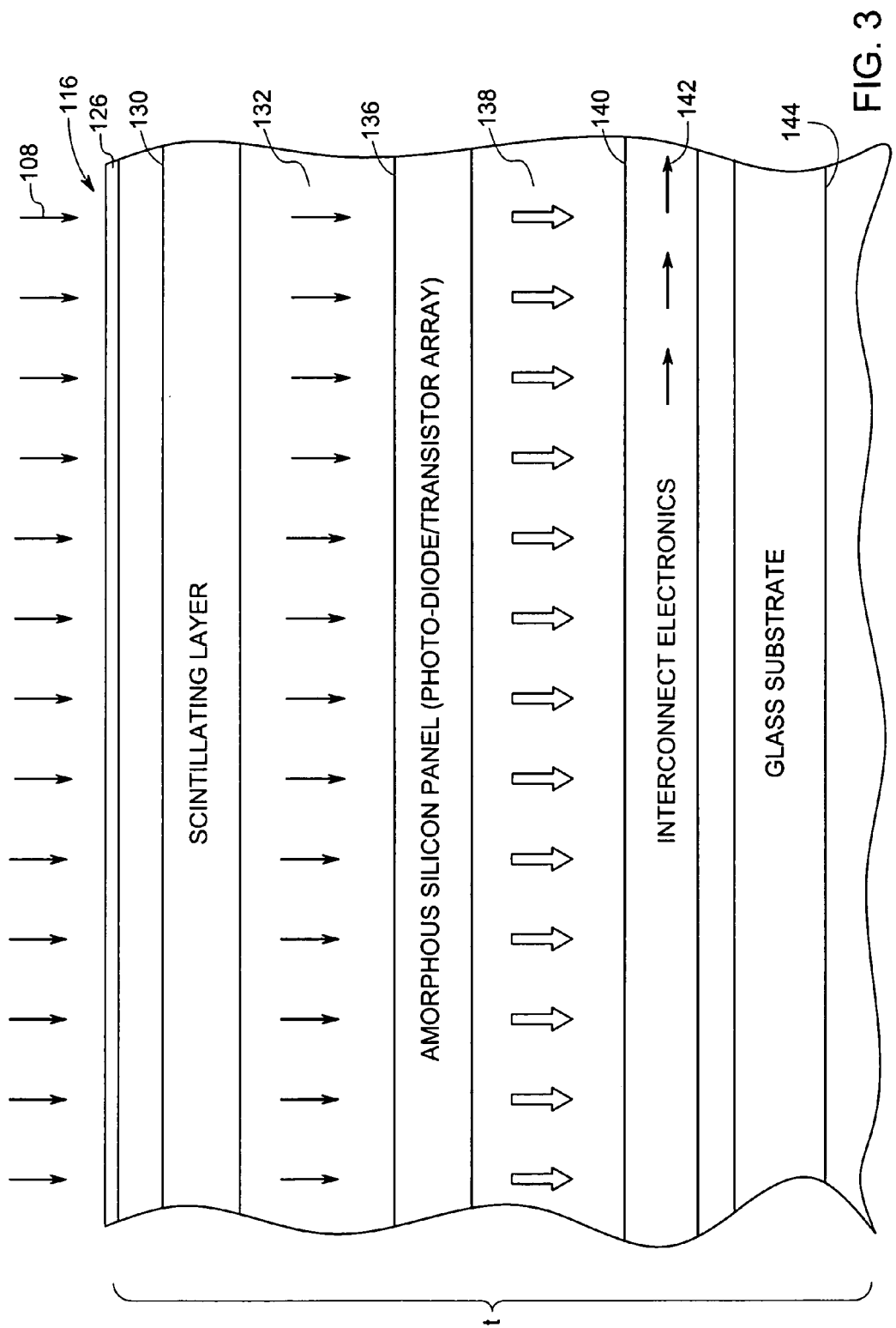
FIG. 3 (PRIOR ART) is an exploded sectional view of the flat panel detector of FIG. 2 taken along line III—III.

FIG. 3 (PRIOR ART) is an exploded sectional view of flat panel detector 116 taken along line III—III of FIG. 2. As illustrated, radiographic image 108 passes through glass plate 126 and is absorbed by x-ray detection panel 134. According to one construction, x-ray detection panel 134 is a single panel x-ray detection panel. X-ray detection panel 134 is an amorphous silicon x-ray detection panel. X-ray detection panel 134 includes scintillating layer 130, which converts x-ray radiographic image 108 into optical radiographic image 132. Scintillating layer 130 is applied through vapor deposition onto x-ray detection panel 134, and in particular to amorphous silicon panel 136. Scintillating layer 130 takes the form of Gadolinium Oxysulfide, Gd2O2S:Tb; or Cesium Iodide, CsI(TI). To receive high energy x-rays, the Cesium Iodide scintillating layer is used.

Amorphous silicon panel 136 is a photo-diode/transistor array that receives and converts optical radiographic image 132 into a plurality of representative image data values 138. Image data values 138 are received in analog form by interconnect electronics 140, and output from panel 136 as analog image data. Scintillating layer 130, amorphous silicon panel 136, and interconnect electronics 140 are formed on silicon glass substrate 144 through semiconductor technology known in the art. Together, scintillating layer 130, amorphous silicon panel 136, interconnect electronics 140, and glass substrate 144 form x-ray detection panel 134.

Figure 4:
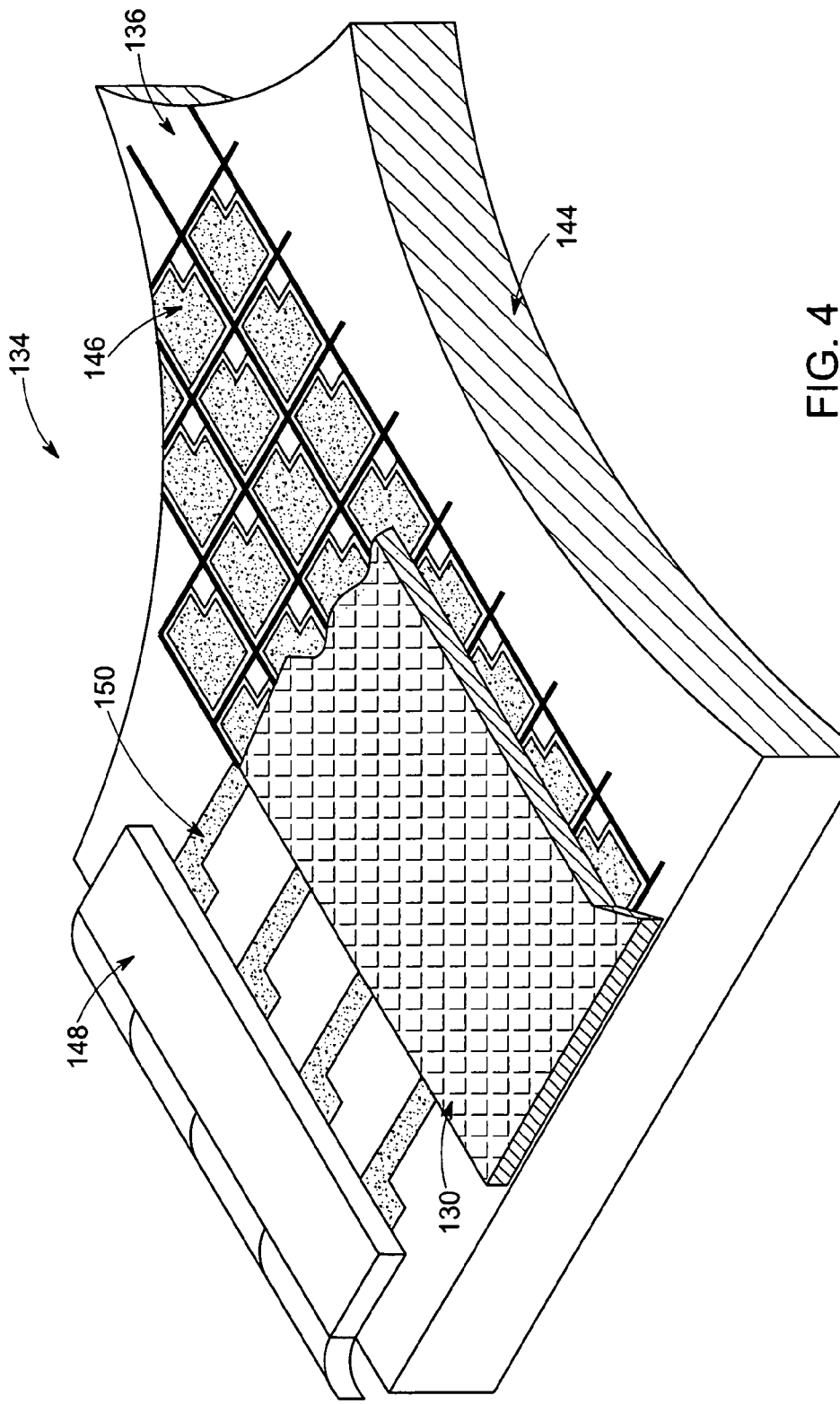
FIG. 4 (PRIOR ART) is an elevated prospective view of an x-ray detection panel removed from a protective metal casing.

FIG. 4 (PRIOR ART) is an elevated prospective view of x-ray detection panel 134 removed from metal casing 128. As illustrated in FIG. 4 (PRIOR ART), amorphous silicon panel 136 forms a plurality of photo cells 146. Electrical information output from each photo cell 146 is transmitted to contact leads 148 by way of a plurality of corresponding contact fingers 150. Contact fingers 150 provide connection between contact leads 148 and amorphous silicon panel 136. As illustrated, scintillating layer 130 is formed on top of amorphous silicon panel 136.

X-ray detection panel 134 provides an array of light sensors with a small spacing between elements, and a large number of elements to adequately receive and detect projected x-ray radiographic images. Amorphous silicon panel 136 is a thin film technology formed on a relatively large glass substrate 144. Eleven layers of amorphous silicon, various metals, and insulators are deposited by plasma enhanced chemical vapor deposition ("PECVD"), sputtering and meniscus coating to form field effect transistors ("FETs"), diodes, interconnects, and contacts. X-ray detection panel 134 forms panels for industrial and medical applications, and in particular, a cardiac/surgical digital x-ray panel, 20×20 cm; a radiography digital x-ray panel, 41×41 cm; and a mammography digital x-ray panel, 19×23 cm. The cardiac/surgical digital x-ray panel has 1024 columns×1024 rows at 200 μm pitch; the radiography digital x-ray panel has 2048 columns×2048 rows at 200 μm pitch; and the mammography digital x-ray panel has 1920 columns×2304 rows at 100 μm pitch.

Amorphous silicon provides a number of advantages over single crystal silicon for the formation of flat panel detectors, and is particularly distinguishable from single-crystal silicon. Amorphous silicon is characterized by having no definite form, and having no real or apparent crystalline structure. On the other hand, single-crystal silicon is grown as a single crystal, sliced into wafers, then polished for further refinement into integrated circuits. Amorphous silicon allows the formation of much larger panels than single crystal silicon because the formation of a single crystal is not used. However, amorphous silicon finds a 100 to 1000 times increase in defects, and a significant reduction in switching speed, which effect signal lag and signal offset characteristics. Scintillating layer 130, CsI(TI), converts x-rays into optical rays and is evaporated onto amorphous silicon panel 136 to provide intimate contact therewith. CsI(TI) forms a needle-like structure, which acts like a plurality of light pipes to prevent lateral spread of the light. Moreover, CsI(TI) provides a transmission spectrum which is well matched to the quantum efficiency of amorphous silicon layer 136.

Figure 5:
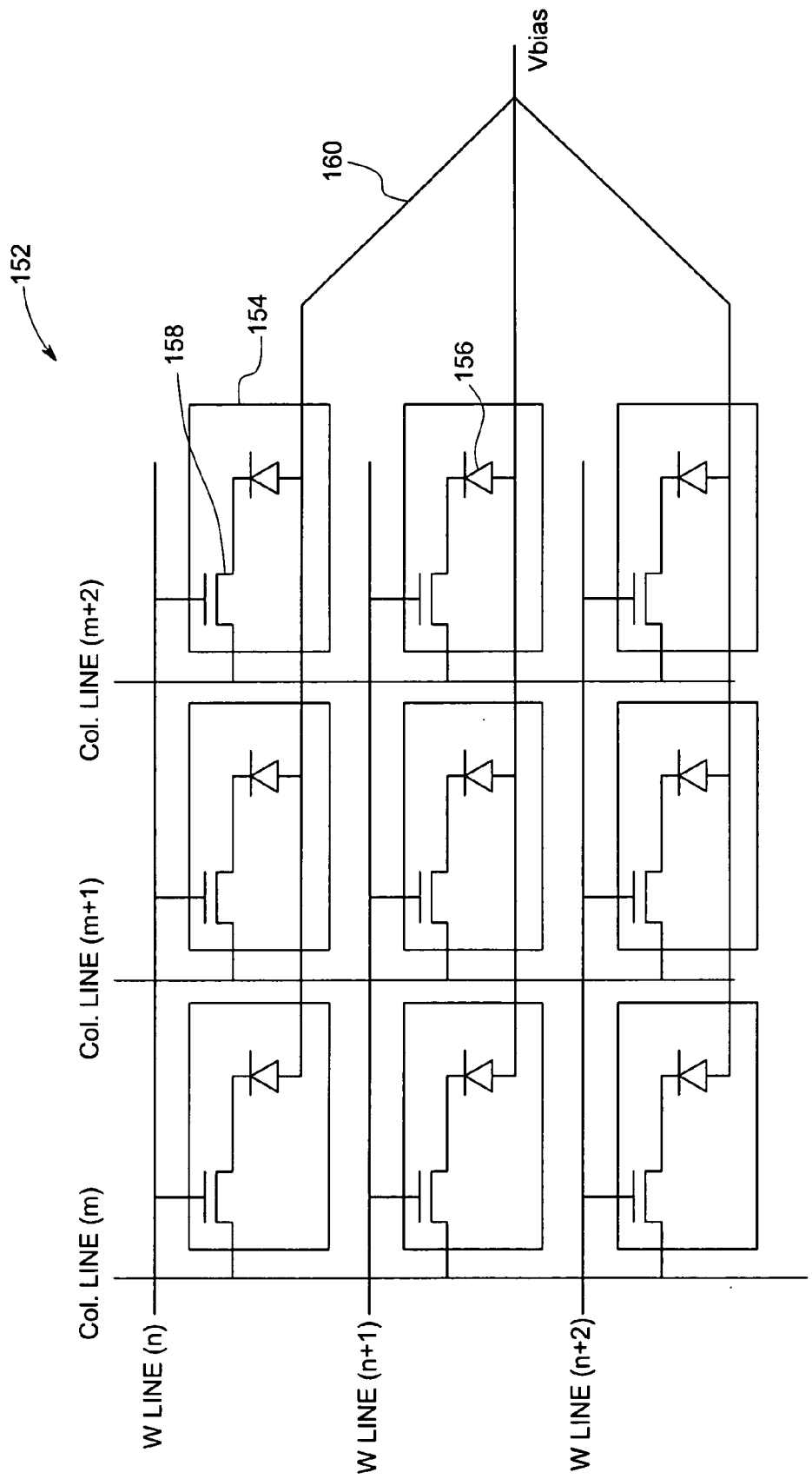
FIG. 5 (PRIOR ART) is a schematic view of a photo cell array formed on an amorphous silicon panel.

FIG. 5 (PRIOR ART) is a schematic view of photo cell array 152 formed on amorphous silicon panel 136. As illustrated, a plurality of photo cells 154 are sequentially triggered in response to a scan from row lines (n), (n+1), (n+2), . . . , etc. Accordingly, corresponding outputs are read out along column lines (m), (m+1), (m+2), . . . , etc. Each photo cell 154 includes a photo diode 156 and a field effect transistor 158. Photo diode 156 is biased by way of bias lines 160 and discharged at the appropriate time by way of field effect transistors 158. The field effect transistors 158 control electrical discharge from the appropriate corresponding column lines. During operation, field effect transistors 158 are turned on by pulsing the appropriate row line to a high voltage, which is pulsed on the order of +11 V. Field effect transistors 158 are turned off by pulling the appropriate row line low, which is on the order of −11 V.

X-ray exposure creates electron-hole pairs in photo diodes 156 of amorphous silicon, x-ray detection panel 134 causing partial discharge. When field effect transistors 158 are then turned on, photo diodes 156 are recharged, and the amount of charge needed to recharge photo diodes 156 is measured. During operation, all row lines are turned off, i.e. to −11 V, during x-ray exposure. The row lines are then sequentially turned on, i.e. to +11 V. Analog to digital conversion of the signals on the appropriate column lines are pipe lined such that the outputs from row "n" are converted from analog information to digital information while row "n+1" is read out. The time period used for analog to digital conversion is on the order of the time used to read out each row line.

Figure 6:
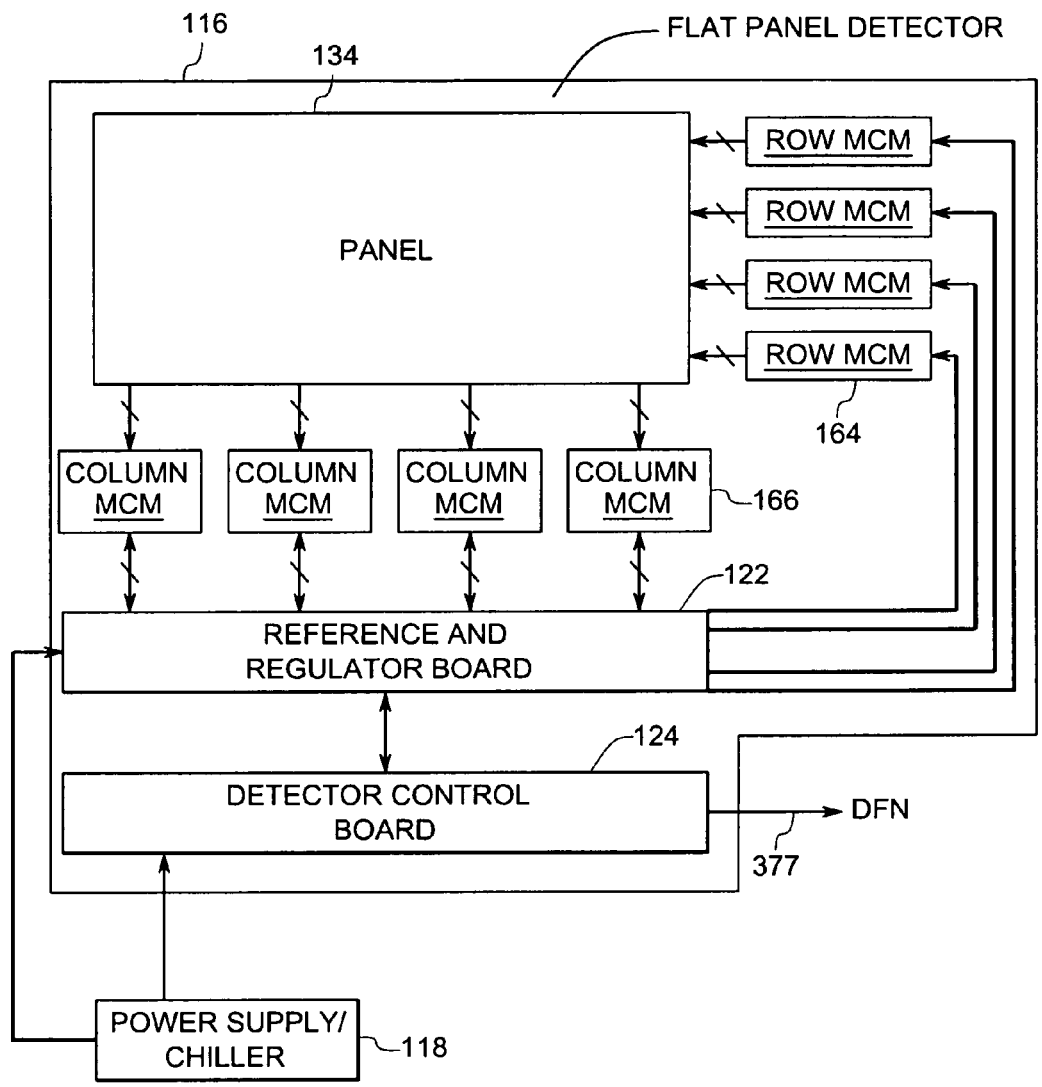
FIG. 6 (PRIOR ART) is a block diagram of an electrical connection in an amorphous silicon single panel detector system.

FIG. 6 (PRIOR ART) is a schematic diagram of electrical connections in flat panel detector 116 according to one construction. Flat panel detector 116 includes a single amorphous silicon, x-ray detection panel 134, electrically coupled to a plurality of row multi-chip modules 164 and a plurality of column multi-chip modules 166. In response to sequential trigger signals from row multi-chip modules 164, all columns are simultaneously read out onto column multi-chip modules 166. Column multi-chip modules 166 convert analog readout signals from detection panel 134 into digital signals, which are in turn received by reference and regulator board 122.

Reference and regulator board 122 combines data output from column multi-chip modules 166 and outputs the same to detector control board 124. In summary, row multi-chip modules 164 turn field effect transistors 158 on and off while column multi-chip modules 166 read out respective column signals. Reference and regulator board 122 supplies voltages to the row and column modules, while communicating control and data signals with respect to detector control board 124.

Figure 7:
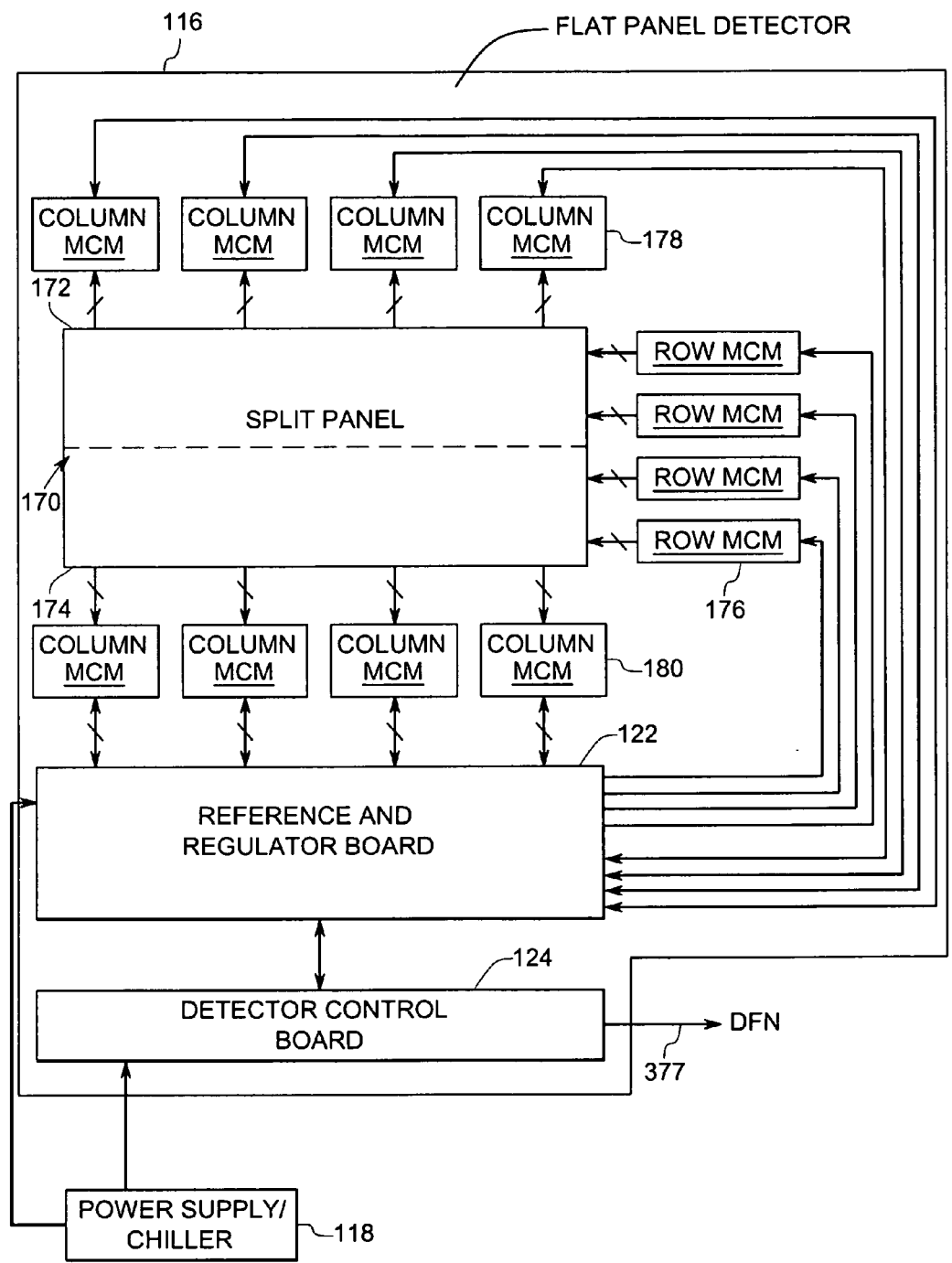
FIG. 7 (PRIOR ART) is a block diagram of electrical connection in an amorphous silicon split panel detector system.

FIG. 7 (PRIOR ART) is a block diagram of electrical connection in flat panel detector 116 according to another construction. Flat panel detector 116 schematically represents electrical connections, such as found in cardiac/surgical digital x-ray panels and radiography digital x-ray panels. As illustrated, flat panel detector 116 includes cardiac/surgical split panel x-ray detection panel 170 having a first panel portion 172 and a second panel portion 174. According to an embodiment of the present invention, split panel x-ray detection panel 170 is a cardiac/surgical split panel x-ray detection panel. First and second panel portions 172 and 174 are respectively triggered by row multi-chip modules 176. The output from first panel portion 172 is received by first column multi-chip modules 178 while the output from second panel portion 174 is respectively received by second column multi-chip modules 180.

FIG. 8 (PRIOR ART) schematically represents one construction of a split panel, such as split panel 170, as a cardiac/surgical digital x-ray panel 182. Cardiac/surgical digital x-ray panel 182 is formed from a first panel portion 184 and a second panel portion 186. Scan lines 0 to 511 appear in first panel portion 184 and also in second panel portion 186. Accordingly, as row scan line 0 is triggered, two row display lines, namely 0 and 1023, are simultaneously activated, and corresponding column output lines are output from first panel portion 184 and second panel portion 186. Likewise, as row scan line 1 is simultaneously activated in first panel portion 184 and second panel portion 186, corresponding column output lines are output from first panel portion 184 and second panel portion 186. As each scan line from each corresponding panel portion is activated, all column output lines from each panel portion output their respective values. Accordingly, as row scan line 0 is activated, column output lines 0 through 1023 are simultaneously output from first panel portion 184 while column output lines 1024 through 2047 are simultaneously output from second panel portion 186.

Figure 9:
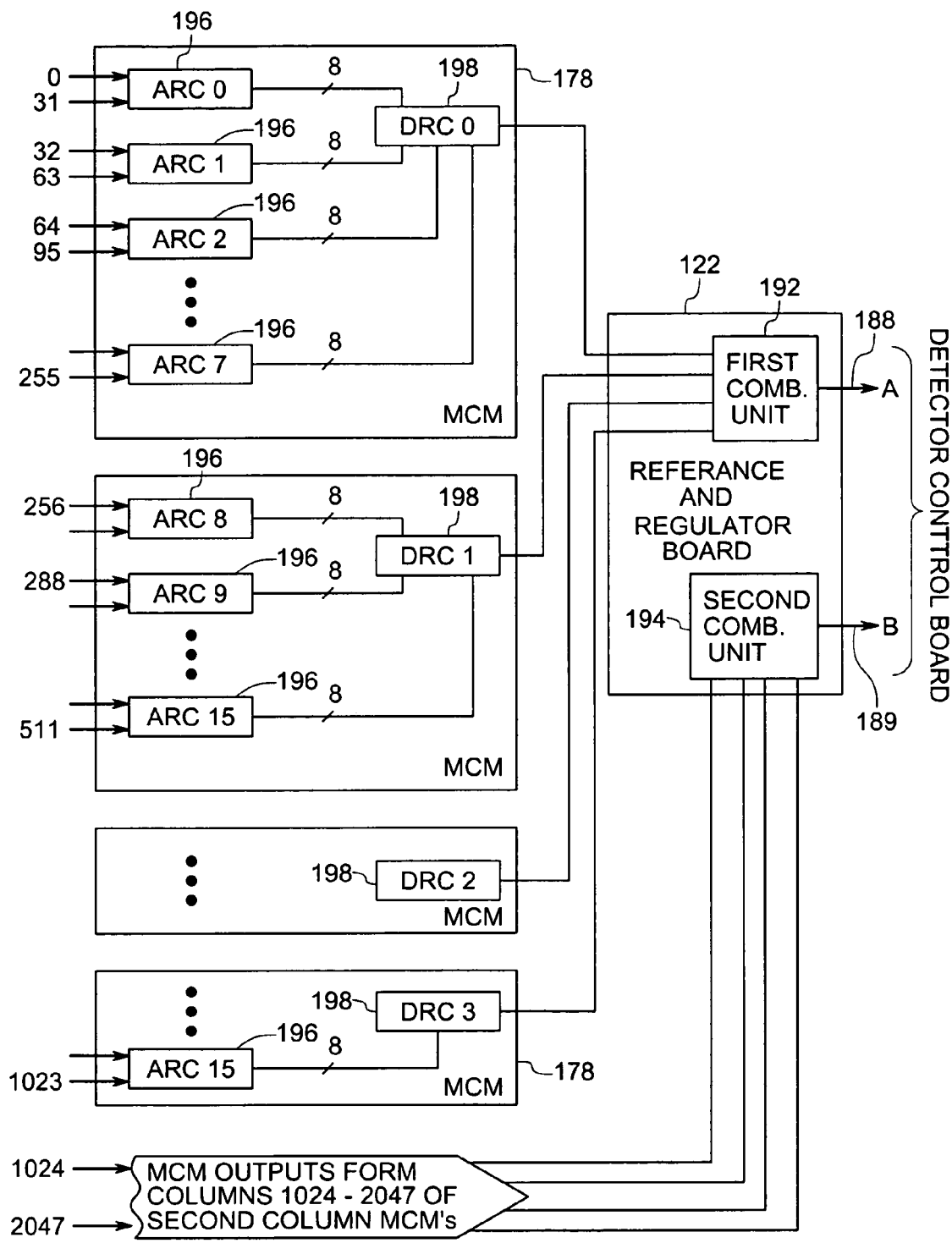
FIG. 9 (PRIOR ART) is a block diagram of column multi-chip modules and a reference and regulator board in a split panel detector system.

FIG. 9 (PRIOR ART) is a block diagram of column multi-chip modules 178 and 180 in conjunction with reference and regulator board 122. Column multi-chip modules 178 receive column signals output from first panel portion 172 while second column multi-chip modules 180 receive the column output signals from second panel portion 174. Accordingly, output from first column multi-chip modules 178 are combined by way of reference and regulator board 122 into combined signal output 188 to be received by detector control board 124. Likewise, column multi-chip modules receive column signals output from columns 1024 through 2047, which are then combined, and transferred to reference and regulator board 122. Reference and regulator board 122 combines the received signals then outputs the combined signal output 189. Collectively, the combined output signals from reference and regulator board, including output 188 and output 189, is output 195.

Reference and regulator board 122 includes first combination unit 192 for combining the outputs from multi-chip modules 178, and also second combination unit 194 for combining the outputs from multi-chip modules 180 corresponding to columns 1024–2047. Each multi-chip module 178 includes eight analog read out chips ("ARCs") 196, which provide a corresponding output to digital read out chips ("DRCs") 198. Thus, the output from the DRCs 198 are received by reference and regulator board 122.

Each ARC chip 196 utilizes a non-linear ramp-compare type analog digital converter. Each ARC chip 196 also receives 32 analog inputs and converts the data into eight channels of multiplexed twelve bit serial, grey scale encoded, data. Each DRC chip 198 then receives the multiplexed twelve bit serial grey encoded data from four ARC chips 196, performs serial to parallel conversion, and converts the grey code into twelve bit binary code. Each ARC chip 196 performs analog to digital conversion on the received data by comparing the signal from each data line in a comparator with a square root encoded ramp generated by a digital to analog converter in common to all channels of all ARCs 196. The ramp voltage is increased in steps at a regular clock rate. When a ramp voltage matches a held voltage, a comparator trips, and a ramp counter value is latched. A time to convert each line of data is at least as great as the clock period times the minimum number of clocks used to convert all received column data lines. A voltage step of the ramp is increased as the signal increases. Quantum noise increases as the square root of each signal, and accordingly the step is increased quadratically so that the step size is a fixed proportion of the noise. By way of the foregoing, interface conditioning of control signals bound for row and column modules use a clock signal on the order of 32.5 MHz, for buffering data output between column modules 178 and 180 and detector control board 124.

Figure 10:
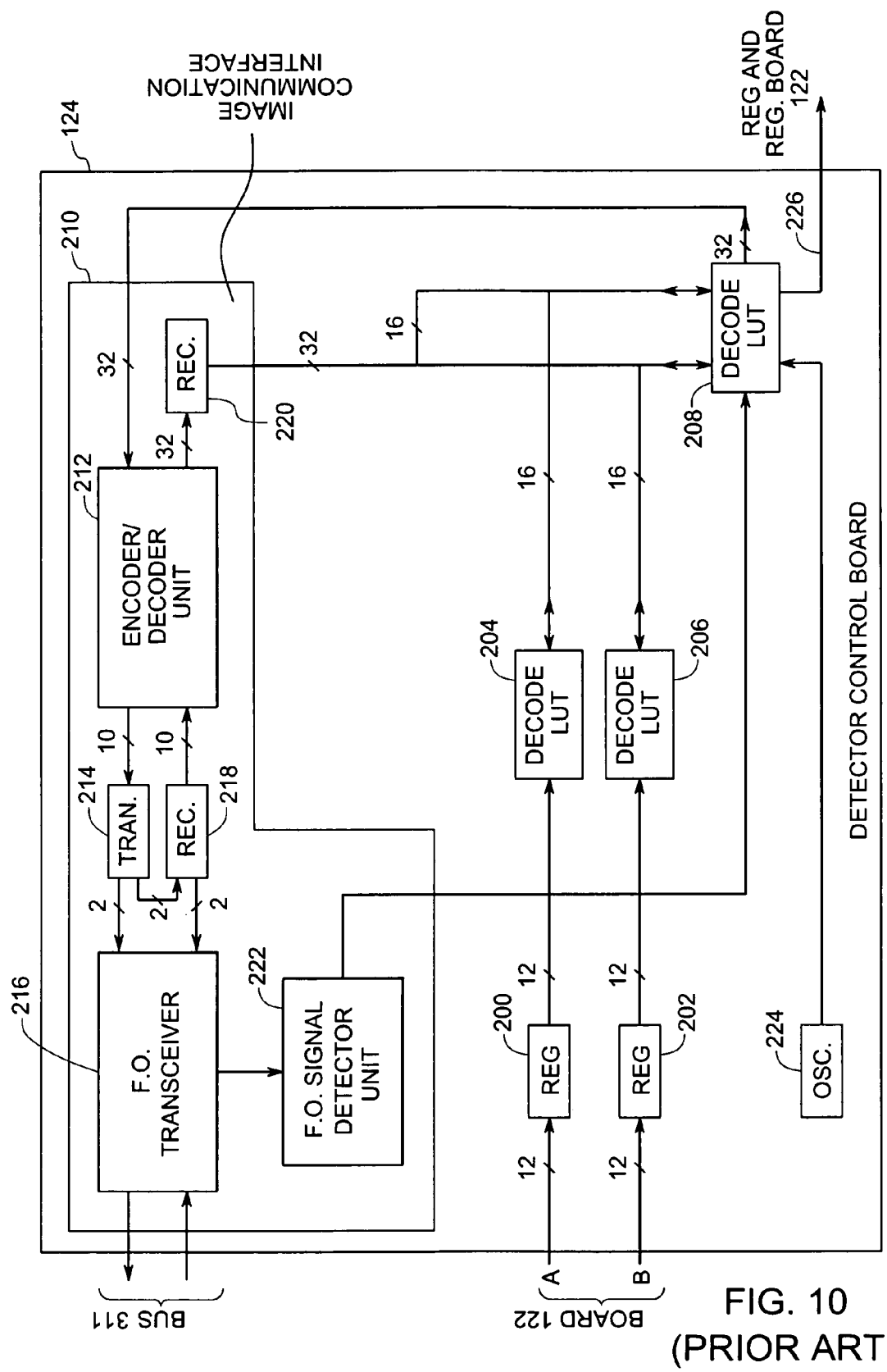
FIG. 10 (PRIOR ART) is a block diagram of a detector control board.

FIG. 10 (PRIOR ART) is a block diagram of detector control board 124. In general, detector control board 124 receives twelve bit binary encoded data "A," corresponding to the output 188 from first column multi-chip modules 178. Detector control board 124 also receives twelve bit binary encoded data "B," corresponding to the output from second column multi-chip modules 180. Each of binary encoded inputs A and B are respectively received by registers 200 and 202. The outputs from registers 200 and 202 are then respectively transferred to decode look up tables ("LUTs") 204 and 206. Decode LUTs 204 and 206 are random access memories that perform a conversion from twelve bit binary quadratically encoded data into 16 bit binary linearly encoded data.

Operation of detector control board 124 is controlled by control unit 208. Control unit 208 is formed as a field programmable gate array ("FPGA"). Control unit 208 receives 16 bit pixel data from decode LUT 204 and 16 bit pixel data from decode LUT 206, then combines the pixel data into a 32 bit word. The 32 bit word is then output to image communication interface 210. According to an embodiment of the invention, image communication interface 210 is a fiber optic interface. Each 32 bit word is a combination of two 16 bit pixels, which were output separately from detector control board 124. The two pixels included in each 32 bit word may be side by side, as in a mammography single digital x-ray panel 224 (set forth in detail below and in reference to FIG. 13 (PRIOR ART)) or may be received from two separate panels, such as output from first panel portion 184 and second panel portion 186 of cardiac/surgical digital x-ray panel 182. Radiography digital x-ray panel 228, set forth below and in reference to FIG. 11 (PRIOR ART), also includes two panel portions 230 and 232, and therefore follows the pixel format of cardiac/surgical digital x-ray panel 182. Split panel detector systems, corresponding to cardiac/surgical digital x-ray panel 182 and radiography digital x-ray panel 228, utilize data "reordering" before display on a conventional computer monitor. Data reordering is set forth in more detail below with regard to detector framing node 304.

Image communication interface 210 clocks 32 bit words received from control unit 208 into encoder/decoder unit 212. Encoder/decoder unit 212 converts each received 32 bit word into four ten bit words, each having error correction. The ten bit words are in turn received by transmitter 214. Transmitter 214 converts the received ten bit words into serial data having two bits, namely a clock bit and a signal bit. Transmitter 214 outputs the two bit data to fiber optic transceiver 216 for conversion into a fiber optic signal. The fiber optic signal is then transmitted on image detection bus 377 to a detector framing node, set forth in detail below. According to one construction, image detection bus 377 is an optical fiber data link. Likewise, fiber optic transceiver 216 receives fiber optic signals from the image detection bus 377 and converts the received optical signals into a two bit data signal for reception by receiver 218. Receiver 218, in turn, converts the received two bit data, including a clock and a data signal, into ten bit words having error correction. The ten bit words are then received by encoder/decoder unit 212 for conversion into 32 bit words, which are stored in register 220 before transmission to control unit 208. An output from fiber optic transceiver 216 is also received by fiber optic signal detection unit 222 to maintain timing and protocol in cooperation with control unit 208. Control unit 208 is clocked by oscillator 224. Control unit 224 provides a control signal to reference and regulator board 122 by way of control line 226. Control unit 208 is preferably a FPGA, Flex 10k50 manufactured by Altec, Inc. of San Jose, Calif.

Figure 11:
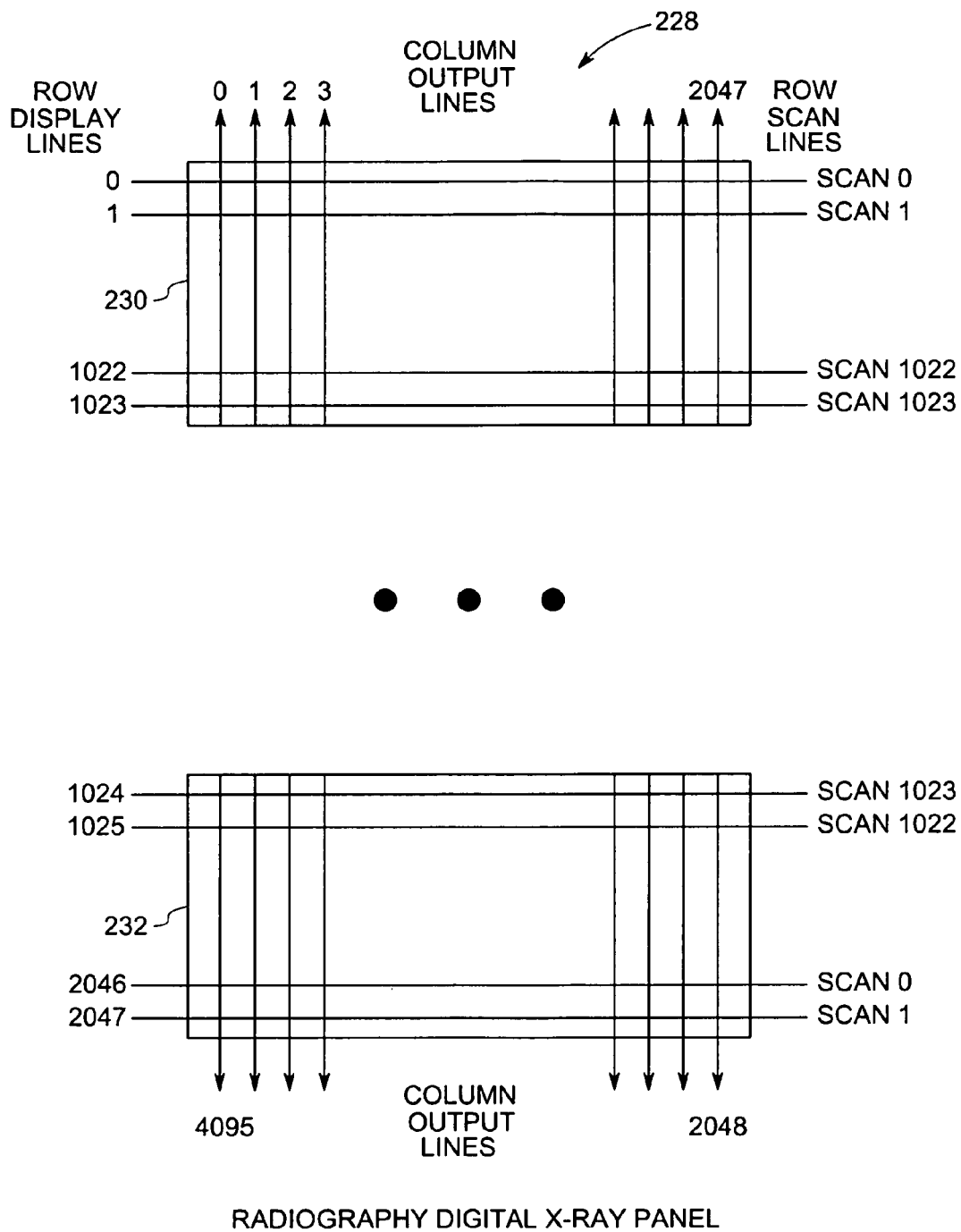
FIG. 11 (PRIOR ART) is a schematic diagram of a split panel radiography digital x-ray panel.

FIG. 11 (PRIOR ART) schematically represents a split panel detector, such as split panel 170, as radiography digital x-ray panel 228. Radiography digital x-ray panel 228 is formed from first panel portion 230 and second panel portion 232. Radiography digital x-ray panel 228 is 41×41 cm and has a total of 2048 columns×2048 rows at 200 µm pitch. According to one construction, flat panel detector 116 has twice as many row multi-chip modules 176 and twice as many column multi-chip modules 180 as the embodiment of FIG. 7. As each scan line is sequentially triggered, all column output lines 0 through 2047 simultaneously release pixel information from first panel portion 230, while column output lines 2048 through 4095 simultaneously release pixel information from second panel portion 232. Radiography digital x-ray panel 228 occupies approximately four times the surface area of cardiac/surgical digital x-ray panel 182. Radiography digital x-ray panel 228 is used for applications requiring a large surface area, such as a chest x-ray, while cardiac/surgical digital x-ray panel 182 finds application in procedures requiring a smaller surface area, such as cardiac fluoroscopy during surgical procedures.

Figure 12:
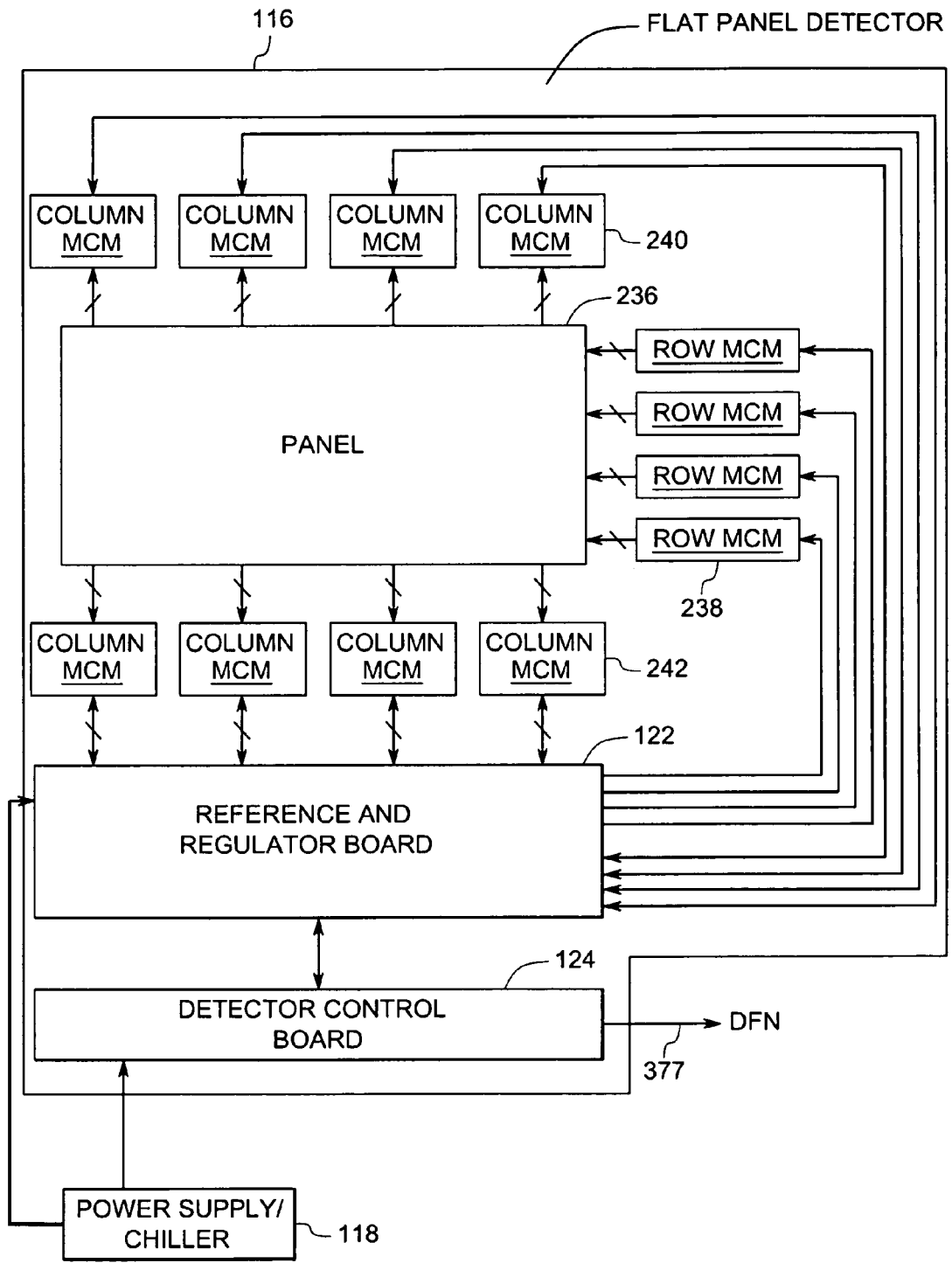
FIG. 12 (PRIOR ART) is a block diagram of electrical connection in an amorphous silicon single panel detector system.

FIG. 12 (PRIOR ART) is a block diagram of electrical connections in flat panel detector 16 according to one construction. Flat panel detector 16 includes single panel 236, which is triggered by row multi-chip modules 238. Single panel 236 is read out by way of column multi-chip modules 240 and 242. Column multi-chip modules 240 and 242 are placed at opposite ends of single panel 236 such that even numbered columns are read out by column multi-chip modules 240 and odd numbered columns are read out by column multi-chip modules 224. Alternate read out of columns from opposite sides of single panel 236 enhances column density by allowing extra physical space for connection of single panel 236 to connecting hardware.

Figure 13:
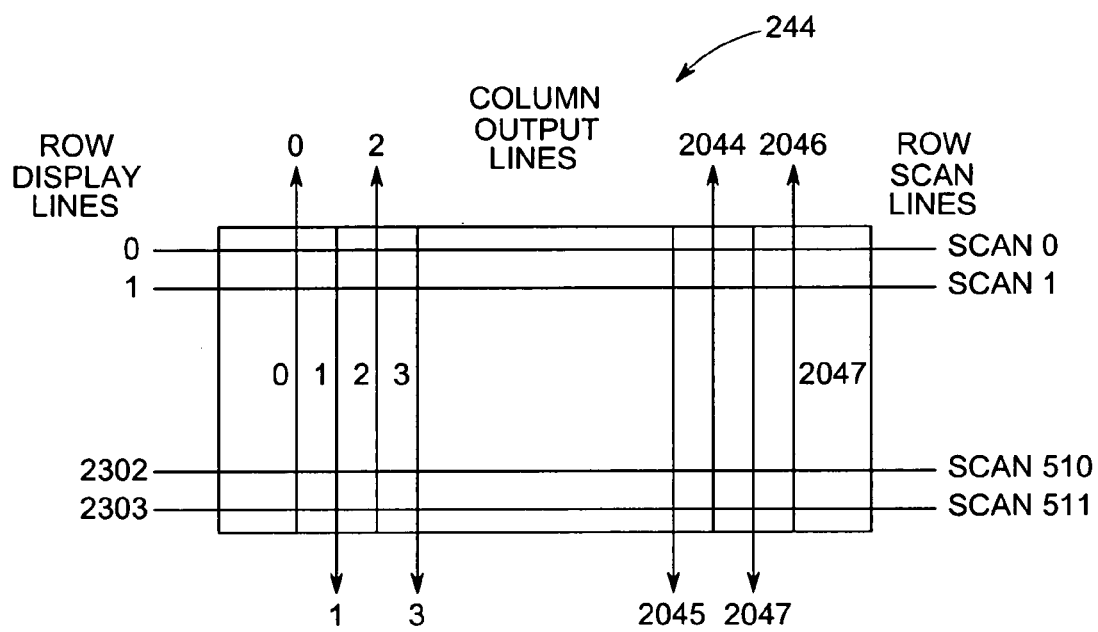
FIG. 13 (PRIOR ART) is a schematic diagram of a single panel mammography digital x-ray panel.

FIG. 13 (PRIOR ART) schematically represents one construction of a single panel detector, such as single panel 236, as a mammography digital x-ray panel 244. Mammography digital x-ray panel 244 is 19×23, cm having 1920 columns× 2304 rows at 100 µm pitch. Mammography digital x-ray panel 244 has a total of 2048 columns. However, 1920 of the available 2048 columns are actually used. The remaining 128 columns are spaced throughout the columns in digital x-ray panel 244 to facilitate repair. Column output lines are alternately output from alternate sides of mammography digital x-ray panel 244. This configuration allows ease in manufacture and simplifies assembly of connecting hardware to the mammography digital x-ray panel 244.

The 128 repair lines included in mammography digital x-ray panel 244 are used to repair open column address lines caused by manufacturing defects. The repair lines cross over both ends of the address lines and are separated by an insulating layer. A repair connection is facilitated by using a laser to weld an address line to a repair line through the insulating layer. In the case of row address lines, the row address lines are fully repaired using spare lines on flat panel detector 116, and therefore the readout system is does not account for the repair. In the case of column repairs, data from repair lines is output in a different sequence from flat panel detector 116 such that the data is sorted by way of post processing.

Figure 14:
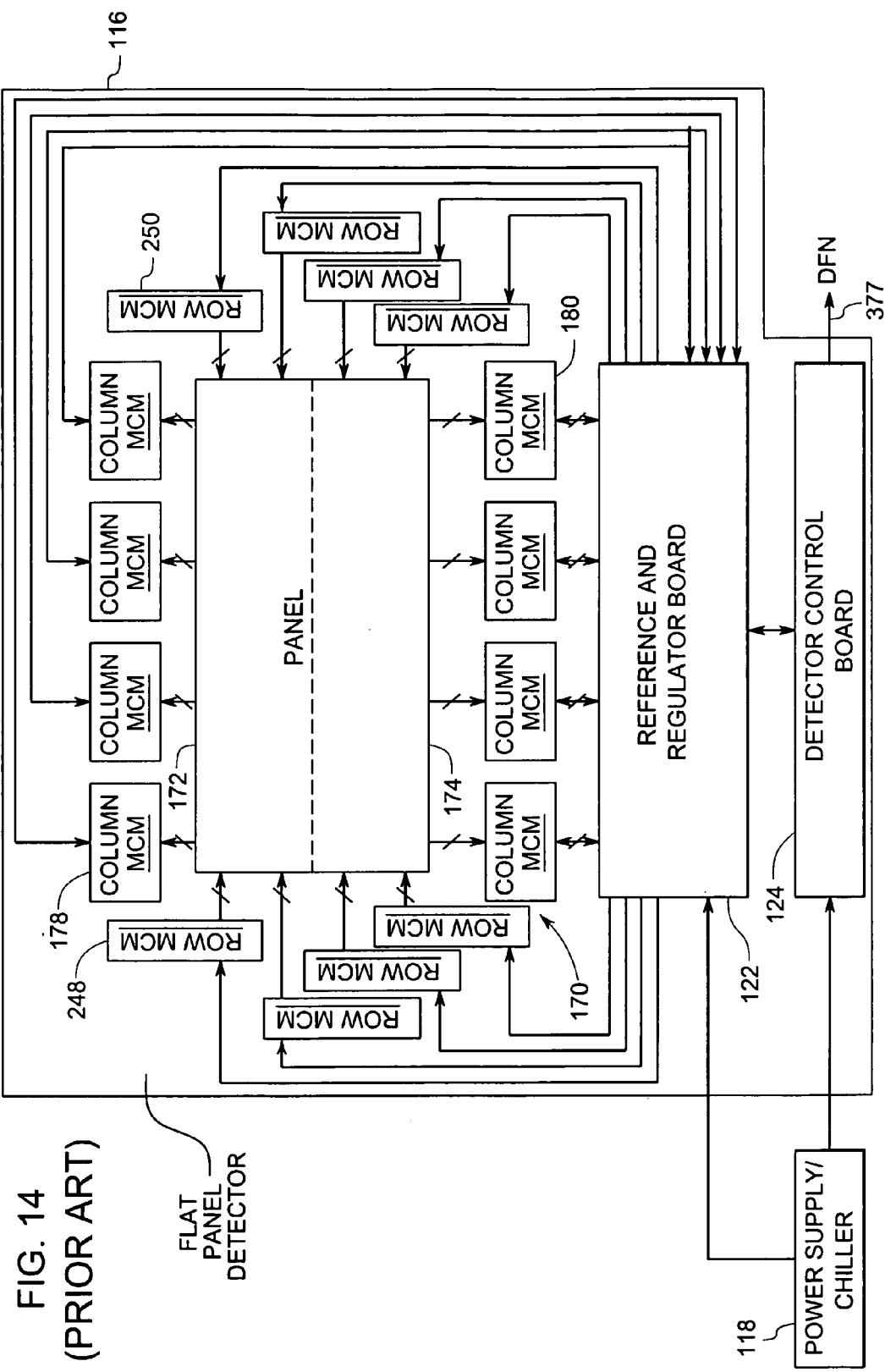
FIG. 14 (PRIOR ART) is a block diagram of electrode connections in a split panel detector system having redundant row multi-chip modules.

FIG. 14 (PRIOR ART) is a block view of electrode connections in flat panel detector 116 according to another construction. Flat panel detector 116 includes two sets of row multi-chip modules, namely first row multi-chip modules 248 and second row multi-chip modules 250. Unlike first and second column multi-chip modules 178 and 180, first and second row multi-chip modules 248 and 250 provide redundant connections across panel rows. Accordingly, if first or second panel portions 172 or 174 develop a defect, each row is optionally triggered from alternate sides thereof, such that data integrity of the row is preserved.

Each construction of flat panel detector 116 set forth above may be formed with redundant row multi-chip modules 250 to preserve data integrity in case of defects in panel formation.

Figure 15:
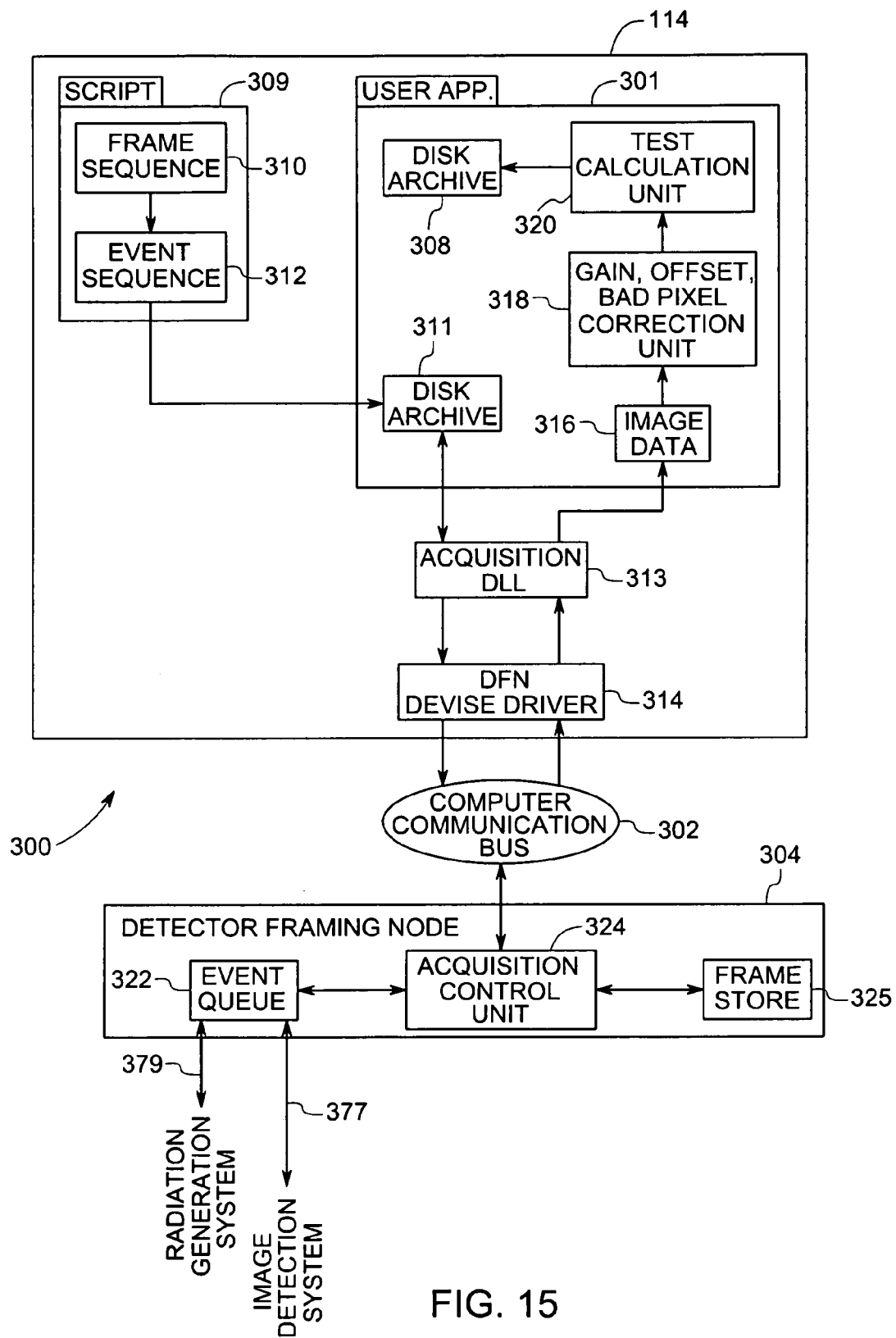
FIG. 15 is a block diagram of control and data flow in an imaging system in which an auxiliary image interface is not utilized.

FIG. 15 is a block diagram of real time radioscopic imaging system 300. System 300 is used in a variety of different medical applications and is also used in engineering, manufacturing, device test and repair. System 300 supports a plurality of different detector panels and particularly supports three different families of detector panel designs, namely for cardiac/surgical, radiography, and mammography applications. System 300 includes host computer 114 running user application 301 from script 309. The user application 301 communication with detector framing node 304 is by way of acquisition DLL 313 and DFN device driver 314.

System 300 replaces a prior Image Detection Controller subsystem ("IDC"), which was based upon a TMS320-C80 processor and PC using real time operating system, VXWORKS® System 300 achieves 30 frames/sec acquisition and processing of 1024×1024 pixel images for fluoroscopy. Image detection bus 377 provides a 1.25 Gbit/sec fiber optic communication link between host computer 114 and detector control board 124. Image detection bus 377 particularly communicates between detector control board 124 of image detection system 112 and detector framing node ("DFN") 304, which preferably is a peripheral component interconnect ("PCI") card suitable for connection to computer communication bus 302. According to one construction, computer communication bus 302 is a PCI bus, and more particularly, a PCI bus operating at 33 MHz. According to another construction, computer communication bus 302 is a PCI bus operating at 66 MHz. Detector control board 124 itself is preferably an Apollo Common Detector Control Printed Wiring Assembly ("PWA"), manufactured by General Electric Medical Systems of Milwaukee, Wis. The Apollo Common Detector Control PWA is used in a variety of applications including full field digital mammography ("FFDM"). Use of detector framing node 304 facilitates use of non-real time host computer 114 for image processing after image acquisition.

System 300 provides acquisition and control based on a commercial single or multiple processor PC hardware, such as the PENTIUM® class processors manufactured by Intel, Inc., of Santa Clara, Calif. System 300 is a single data acquisition and control system for present and anticipated x-ray modalities, and supports application of the system to both engineering and manufacturing. A flexible architecture is provided to address needs of improved or future technology.

System 300 supports single and multiple frame acquisition of images with frame to frame control of supported detector parameters. A number of rows and a number of columns in an acquired image are supported as input parameters, while providing control of data acquisition timing from an external frame trigger. System 300 acquires and views gain and offset corrected images at 30 frames/sec for a 1024×1024 array or 7.5 frames/sec for a 2048×2048 image. System 300 supports a non-real time operating system to test system functionality. According to an operative configuration, the non-real time operating system is WINDOWS NT 4.0® supporting C++ language based applications. Modular software is structured to support a combination of applications and more direct hardware access for advanced users and programmers. User-coded test applications and generalized data acquisition routines are provided in separate modules.

System 300 provides archive capability for both raw, and gain and offset corrected data for single and multiple frames, including regions of single and multiple frames. A high resolution display of single and multiple frames and for regions of single and multiple frames is supported for both freshly acquired and archived data. Control of radiation generation system 109 or a grid controlled x-ray tube is supported through a real time bus interface. Real time triggering of the x-ray generator with 2μ sec timing resolution is supported along with programmable time delays of up to 16 seconds.

System 300 is a real time image data acquisition system in which the image data is acquired at a predetermined frame rate and the number of image frames to be acquired is determined at the time of acquisition. Before acquisition, the event compiler 408 sets up the frame rate by setting a time for executing a repetitive trigger over the real time bus 379. Likewise, the event compiler 408 sets up image acquisition by delaying the image request command to the image detection system 112 from the repetitive trigger. There is an integration period before scanning of the flat panel detector 116 is allowed to account for delays in the phosphor and collection of electron-hole pairs in the photodiode array. For real time data acquisition, there is minimal buffering during transfer of the image data from the image detection system 112 to the detector framing node 304, such that the image detection system 112 and the detector framing node 304 operate in synchronism.

According to one construction, system 300 is configured as follows:

Computer: Single/multiple PENTIUM® class with PCI back-plane
Operating System:WINDOWS NT 4.0®
Panel Designs: Apollo20: 1024×1024—Data Reordered
Apollo40: 2048×2048—Data Reordered
Mammo3: 2304×2048—Bad column corrected
Smaller regions of interest
Acquisition Modes: Radiographic (isolated frames)
Real Time (30 frames/sec for 1024×1024 image)
Cine Loop (30 frames/sec for 1024×1024 image)
Hardware debug
Image processing: Offset, Gain, Bad pixel, Mammography bad column
Display Req.: 8 bit gray scale including gamma correction
Real time window and level
Xia type display applications including zoom and pan
X-ray support: Simple 8 bit parallel real time bus
Archive support: Hard drive and writable CD ROM drive System 300 provides an improvement over the above prior IDC test system. Real time parameters, which were previously addressed in prior art VXWORKS® operating system ("OS"), are now captured in detector framing node 304 operatively embodied as a single PCI card. Detector framing node ("DFN") 304 contains fiber channel communication circuitry, a buffer memory, a PCI communications controller, a real time bus to control the x-ray generator and a set of firmware programmable FPGAs for control of all circuits on DFN 304. An external PCI memory card is used in conjunction with DFN 304 to expand computer memory and provide storage for raw pixel x-ray image data. Operation of data acquisition and subsequent data processing is through user written applications. A library of functions access hardware functionality and facilitate disparate needs of users in engineering, device repair and manufacturing areas.

FIG. 15 particularly illustrates operation of system 300, whereby this system does not include an auxiliary image interface (to be described in detail in a later portion of this application). An exact sequence of image frames and associated acquisition parameters is needed in advance for a particular image acquisition. Accordingly, one can specify, for each frame, the readout delay relative to x-ray pulse, the detector parameters, etc. A description of such attributes is captured in a frame sequence 310 of script 309. Program applications configure the data acquisition system through the frame sequence structure and then trigger the system to initiate acquisition of the frames. The frame sequence 310 will vary depending on the type of experiment being performed for each test. At a hardware level, the acquisition itself responds to a sequence of instructions from host computer 114. According to an embodiment of the present invention, the instructions are event instructions, known collectively as an event sequence 312. Each event instruction is executed at well-timed intervals. Event instructions trigger events that control external devices, such as through commands communicated over bus interfaces. For example, event instructions include 32 bit control words that are sent over image detection bus 377 to image detection system 112, and x-ray pulse trigger commands sent over real-time bus 379 to radiation generation system 109. Based on frame sequence 310, a complete list of such event instructions to be performed is constructed. The event sequence 312 need not be constructed in real-time and is therefore easily executed on host computer 114 running a non-real time operating system to support an event compiler. Once the event sequence 312 is known, the details are transmitted to DFN 304 for execution in real-time.

FIG. 15 shows the flow of control information and data through system 300 during image acquisition. As illustrated, frame sequence 310 is created by way of script 309. Frame sequence 310 is then translated into event sequence 312 using a compiler, which knows the details of the target control hardware. Event sequence 312 is received by test control unit 311, then sent to DFN device driver 314, over computer communication bus 302, and finally to detector framing node 304. The event sequence 312 is then stored in preparation for execution. Event sequence 312 is initiated by sending a Begin Sequence command over computer communication bus 302. The extent of real-time control allotted to host computer 114 is confined to a determination of when event sequence 312 will begin. Subsequently, host computer 114 is completely removed from image acquisition.

Once event sequence 312 is complete, host computer 114 retrieves the acquired data in addition to various diagnostics and responses, which were recorded during execution of the event sequence. Therefore, host computer 114 is involved in pre- and post processing roles, and is therefore entirely removed from real-time operation.

As illustrated, detector framing node 304 communicates commands and responses with computer communication bus 302 by way of acquisition control unit 324. Event sequence 312 is communicated to event queue 322 by way of acquisition control unit 324. Event instructions are then transmitted to radiation generation system 109 from event queue 322. During application of the radiation, event instructions are transmitted to event queue 322 from image detection system 112. Radioscopic image data is also received by frame store 325 from image detection system 112, then transmitted to acquisition control unit 324 for transmission to host computer 114. In host computer 114, image data 316 is transferred through DFN device driver 314 and acquisition dynamic link library ("acquisition DLL") 313 before being subject to gain, offset, and bad pixel correction by gain, offset, and bad pixel correction unit 318. After completion of the correction, the image data is interfaced with test calculation unit 320 before being sent to disk archive 308.

Figure 16:
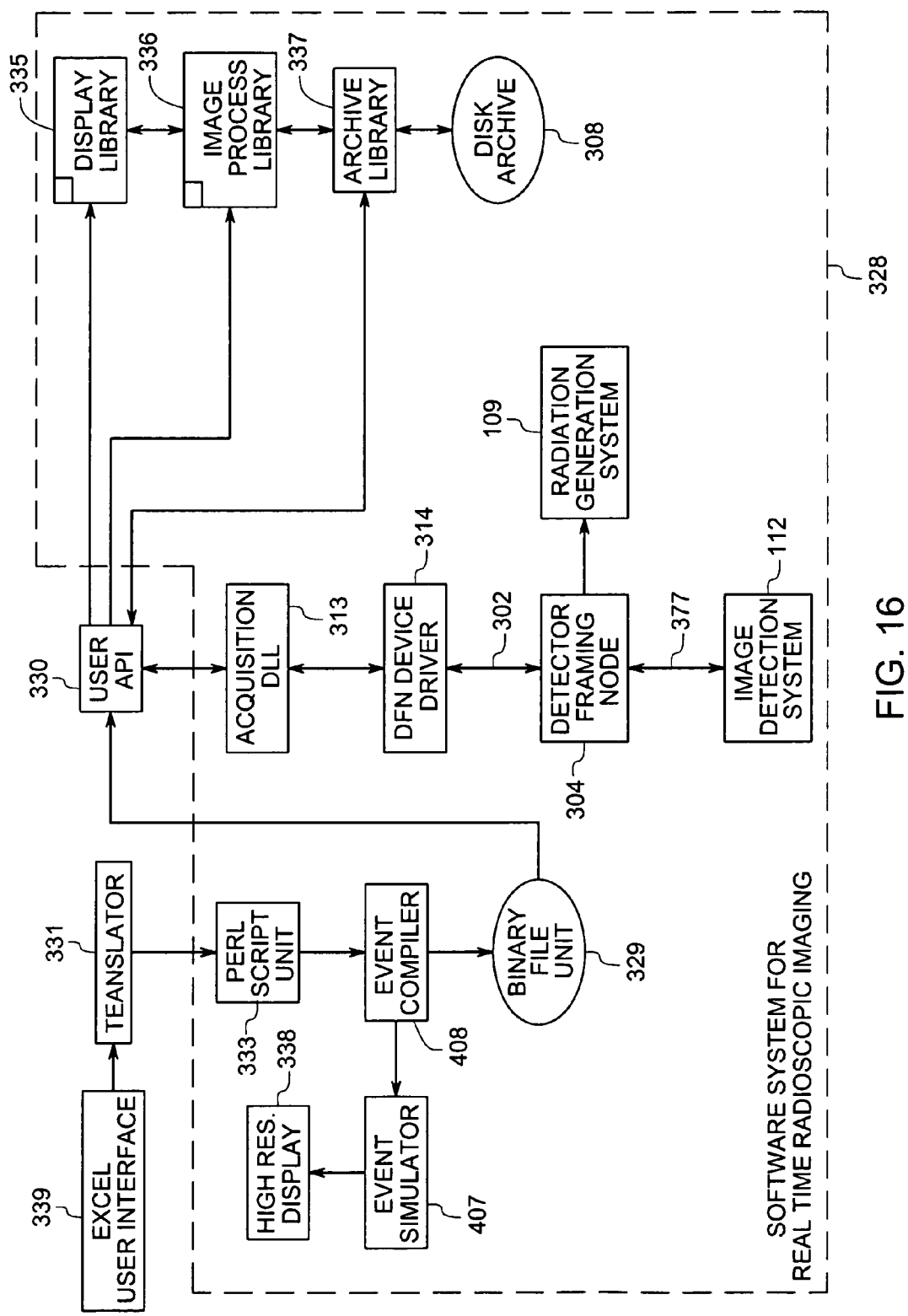
FIG. 16 is a block diagram of a software system for real time radioscopic imaging.

FIG. 16 is a block diagram of a software system 328 for real time radioscopic imaging. User application interface ("API") 330 is software, which runs on host computer 114 and links acquisition hardware to user application 301. Acquisition DLL 313 is software communicating with elements within software system 328. Acquisition DLL 313 communicates bi-directionally with user API 330 and DFN device driver 314. As illustrated, DFN device driver 314 communicates bi-directionally with detector framing node 304, which in turn communicates with radiation generation system 109 and image detection system 112. User API 330 also communicates with display library 335, image process library 336 and archive library 337.

For communication with software system 328, instructions are prepared in excel user interface 339, and then translated by translator 331 before being received by Perl script unit 333. Event compiler 408 also outputs information to binary file unit 329. The output from binary file unit 329 is then loaded into EAB memory 474 on EP 374 under control of user API 330, Acquisition DLL 313, and DFN device driver 314. The binary file contains information to control event sequence 312. Event sequence 312 can be debugged on the high resolution display 338 be creating the timing information in the event simulator 407.

Figure 17:
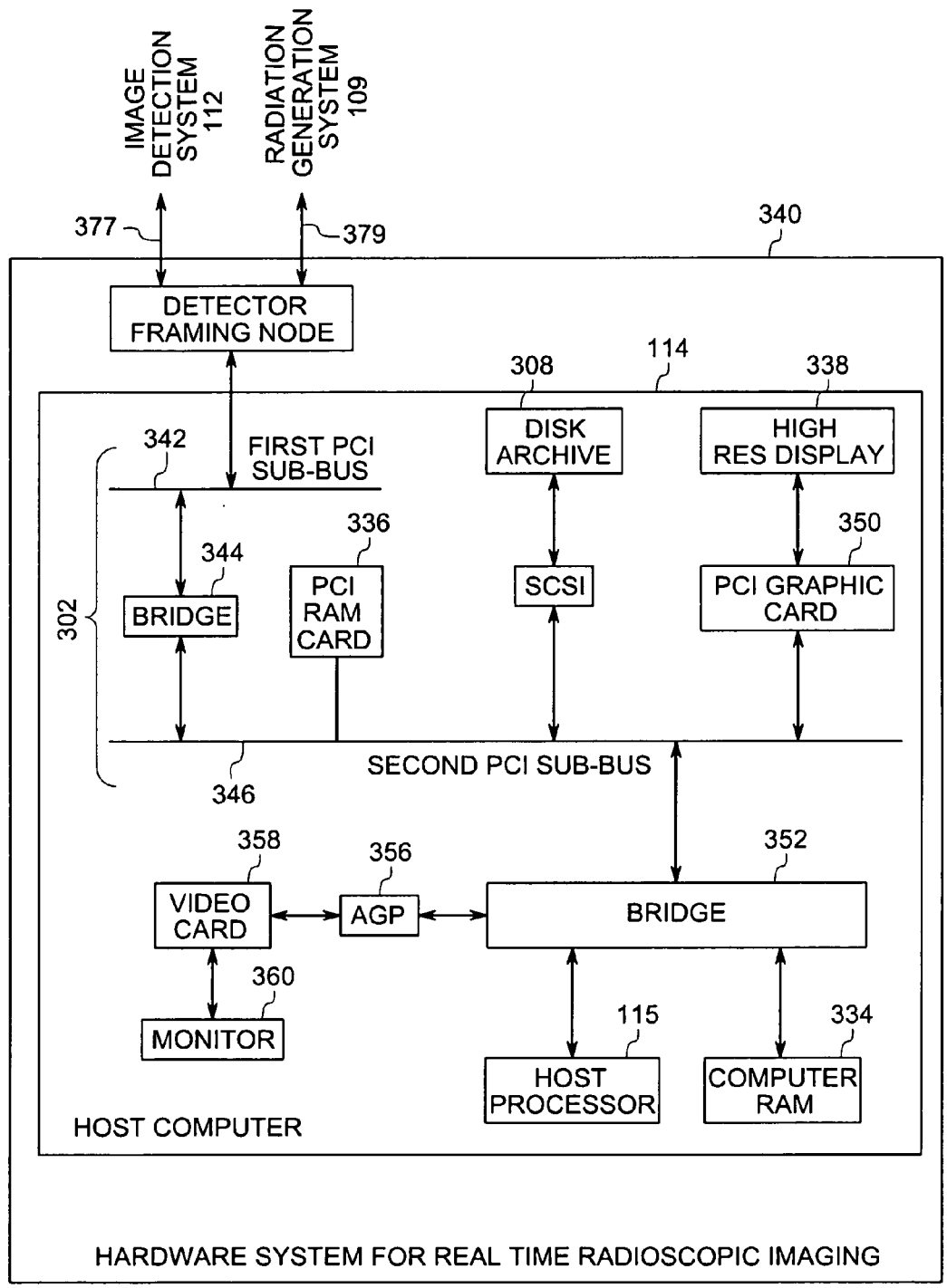
FIG. 17 is a block diagram of a hardware system for real time radioscopic imaging.

FIG. 17 is a block diagram of a hardware system 340 for real time radioscopic imaging. Hardware system 340 includes data acquisition and control hardware. Hardware system 340 is also a block diagram of tester hardware. Except for detector framing node 304, remaining hardware components are commercial off-the-shelf ("COTS"). Host computer 114 is controlled by host processor 115. According to another embodiment of the present invention, host processor 115 is formed as a pair of processors operating together. According to yet another embodiment of the present invention, host processor 115 is formed as a plurality of interconnected processors. Host memory 117 is formed by computer RAM 334 and PCI RAM card 336 set forth in greater detail below. Hardware system 340 receives data of 1024×1024 images (2 MByte) at 30 frames/sec, which corresponds to a data transfer rate of 60 MBytes/sec. Computer communication bus 302 has a transfer rate of 132 MByte/sec. Because of arbitration of first PCI sub bus 342, the transfer rate across computer communication bus 302 is less than 132 MByte/sec.

Hardware system 340 includes DFN 304, which is connected to computer communication bus 302. Computer communication bus 302 is comprised of first PCI sub bus 342 and second PCI sub bus 346, connected by bridge 344. Second PCI sub bus 346 interconnects with disk archive 308 by way of small computer systems interface ("SCSI") 348. Second PCI sub bus 346 also connects to high resolution display 338 by way of PCI graphics card 350. Second PCI sub bus 346 connects to host processor 115, accelerated graphics port ("AGP") 356 and computer RAM 334 by way of bridge 352. AGP 356 is a high speed graphics port for connection of monitor 119 by way of video card 358.

In a real time mode, PCI 302 bus arbitration will slow the data transfer rates on first PCI sub bus 342 and second PCI sub bus 346 such that the continuous display rate of 30 frames/sec will likely be determined by arbitration conflicts. In hardware debug mode, a test of DFN hardware is started from host processor 115 by sending a Command to DFN 304. The results of this test (i.e. bad, good) are returned to host computer 114. This hardware debug mode is used to run the Built-in-self test ("BIST") described later in the specification. In real time mode, data is sent directly from a buffer memory on the DFN 304 to computer RAM 334 and displayed almost simultaneously.

Figure 18:
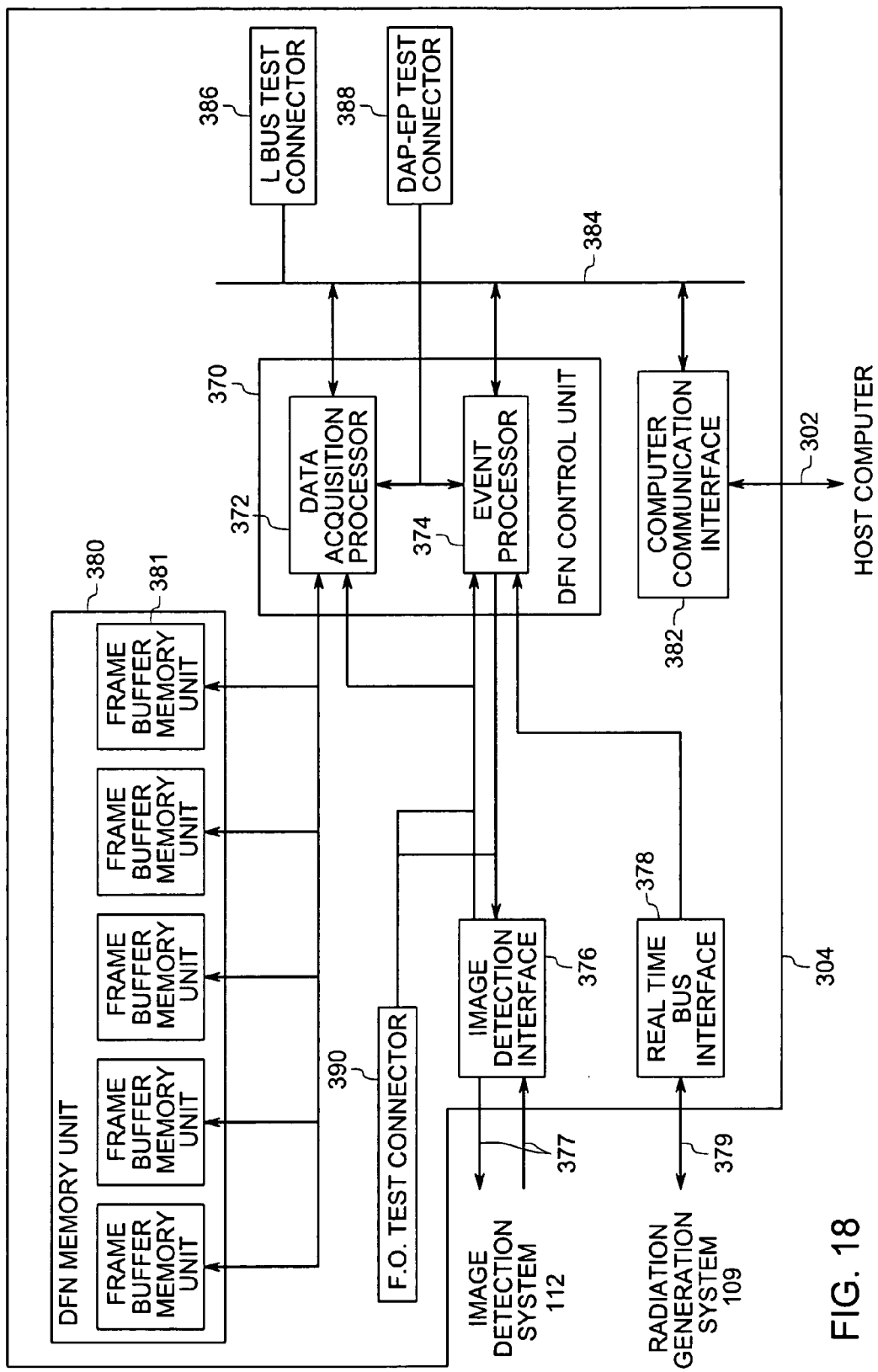
FIG. 18 is a block diagram of a detector framing node.

FIG. 18 is a block diagram of detector framing node 304. Image detection interface 376 communicates with detector control board 124 (described above with reference to FIG. 10 (PRIOR ART)) to receive image data therefrom. According to an embodiment of the present invention, image detection interface 376 is a fiber optic interface. DFN memory unit 380 includes a total of ten 8 Megabit SRAMs. DFN memory unit 380 includes five frame buffer memory units 381, with each frame buffer memory unit 381 comprising two 8 Megabit SRAMs. When one frame buffer memory unit 381 becomes full the data is read out of that unit to computer communication bus 302 and data is then written to another frame buffer memory unit 381. A large image, such as 2048×2048, is read directly into DFN memory unit 380 with data reordering occurring during a data write under control of data acquisition processor ("DAP") 372. DAP 372 and event processor ("EP") 374 are FPGAs, which are used to control real-time bus interface 378. Real time bus interface 378 is connected to real time bus 379. EP 374 also controls read and write of data with respect to image detection bus 377 by way of image detection interface 376. Computer communication interface 382 is embodied as a PCI interface in the form of an application specific integrated circuit ("ASIC") to control bus communications between local bus 384 and computer communication bus 302. As illustrated, fiber optic test connector 390 interfaces with the bus connecting image detection interface 376 and DFN control unit 370.

Imaging system 100 provides support for several different users, including support for different x-ray image panel designs and applications. Accordingly, flexible testing is provided to support different image acquisition modes. The acquisition modes used by imaging system 100 are described in terms of the target applications and users. For example, support for, at least, four specific modes is presented Hardware Debug, Panel Setup, Single Frame, and Real Time. However, modal capability of imaging system 100 is more generically specified in terms of data management and bandwidth considerations.

Figure 19:
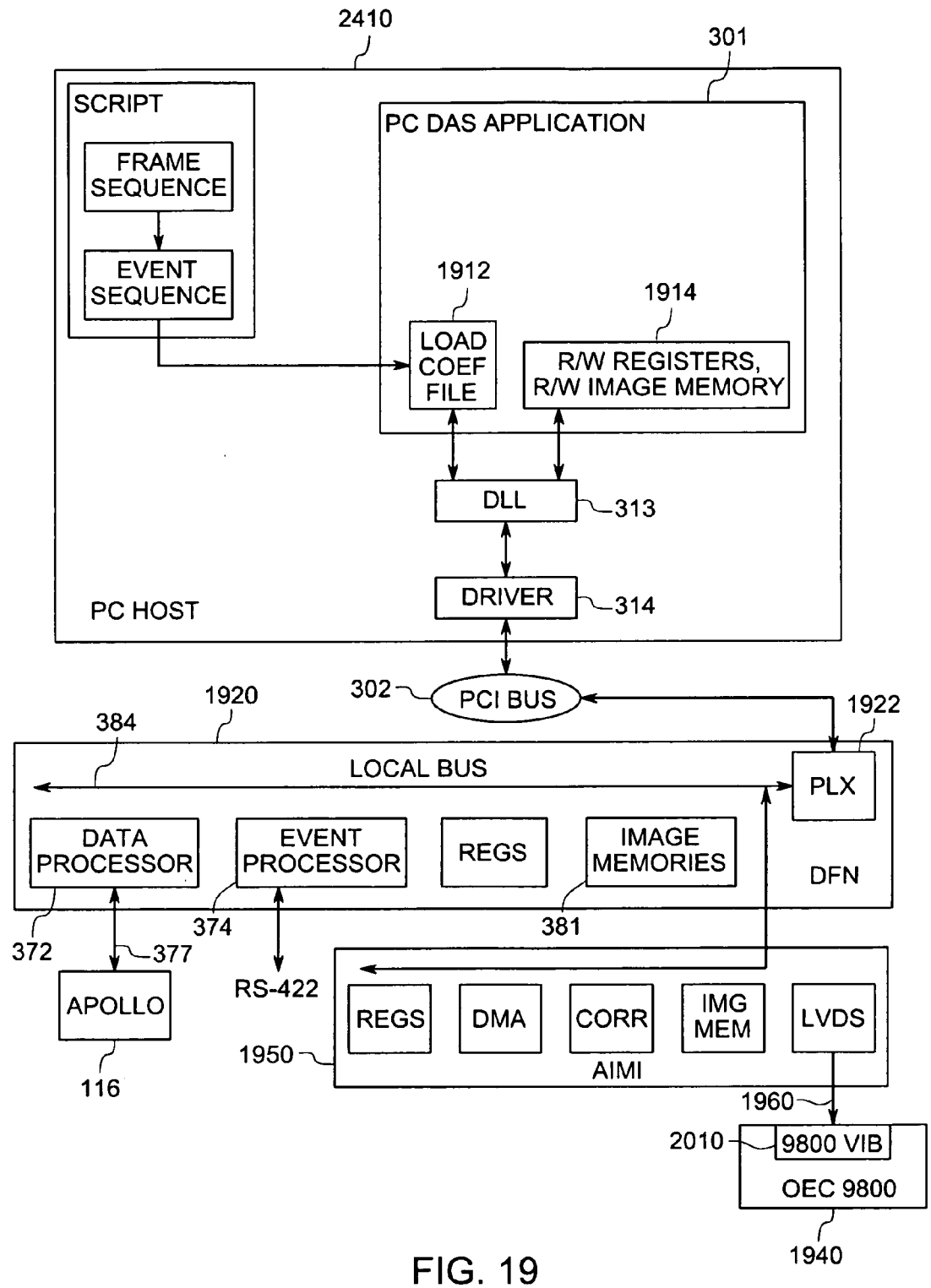
FIG. 19 is a block diagram of a system according to a first embodiment of the invention, in which an auxiliary image interface is provided to convert received x-ray data into a format that can be processed by an OEC 9800 unit.

FIG. 19 is a block diagram showing system dataflow in an imaging system according to a first embodiment of the invention, in which an auxiliary image interface (AIMI) card is provided to convert received x-ray data in an appropriate format to be processed and displayed by an OEC 9800 unit. As explained earlier, the OEC 9800 unit is a mobile C-arm product for cardiovascular, orthopedic and surgical imaging. The use of the AIMI card provides an interface for imagery data to the OEC 9800 unit.

The PC host 2410 shown in FIG. 19 is similar to the Host Computer 114 shown in FIG. 15, whereby element 301 is shown in a somewhat different format with Load COEF file unit 1912 and with R/W registers and R/W image memory

1914. The DFN 1920 shown in FIG. 19 is similar (but with different firmware) to the DFN 304 shown in FIG. 18, whereby PLX 1922 corresponds to Computer Communication Interface 382. The Apollo detector 116 corresponds to the Flat Panel Detector 116 shown in FIG. 1. The OEC 9800 unit 1940 is not shown in any previous figures, and it communicates directly with the AIMI card 1950, whereby the AIMI card 1950 retrieves image data from buffers of the DFN 1920, converts the retrieved image data to a different format, and sends the reformatted image data to the OEC 9800 unit 1940 over Low Voltage Differential Signaling (LVDS) lines 1960, whereby the converted data is in a format that the OEC 9800 unit 1940 can accept (and thereby process).

The present invention as shown in FIG. 19 provides a way by which the Apollo (20 cm) detector 116 may be integrated with the OEC 9800 unit 1940 for clinical trials (and thereafter for clinical use if the trials are successful).

Figure 20:
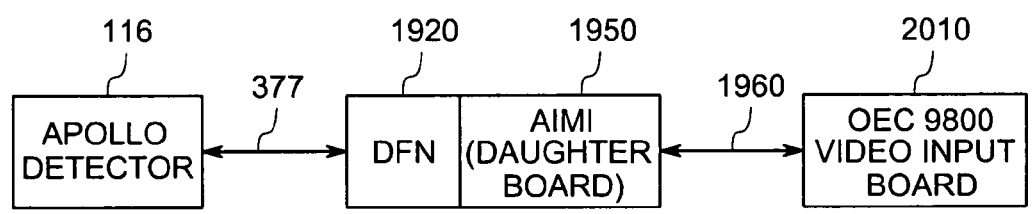
FIG. 20 depicts the image flow from the Apollo (20 cm) detector to the OEC 9800 unit, according to at least one embodiment of the invention.

FIG. 20 depicts the image flow from the Apollo (20 cm) detector 1116 to the OEC 9800 unit 1940 (shown by way of the OEC 9800 Video Input Board 2010), which is the element of the OEC 9800 unit 1940 that receives input data from the LVDS lines 1960. In a first mode of operation, the DFN 1920 outputs image data to PC host memory (see element 114 in FIG. 15) via a DMA over the PCI Bus (see computer communication bus 302 in FIG. 15). However, the OEC 9800 unit 1940 desires the data to be input via a custom electrical connection on the OEC 9800 video input board 2010 and desires the data to be in a format similar to that output from a CCD camera with V-Sync, H-Sync, and Clock. The AIMI 1950, which is also referred to as the DFN daughter card, formats the data and communicates it to the OEC 9800 video input board 2010 via a dedicated electrical signal. Additionally, there is some control information exchanged between the OEC 9800 unit 1940 and the DFN 1920. Furthermore, the AIMI 1950 is provided with ample computational power to assist the OEC 9800 unit 1940 in panel corrections for the Apollo Detector 116, if necessary.

FIG. 21 shows a format 2100 for a first preferred mode in which data is provided to the OEC 9800 unit 1940, whereby the AIMI 1950 converts imagery data obtained from the DFN 1920 (which itself obtained the data from the Apollo Detector 116) into the particular format shown in FIG. 21. This format is the same format that image enhanced data is provided by way of a CCD camera (not shown) to the OEC 9800 unit 1940 in its current configuration. By utilizing the same format, the Apollo detector 116 can provide x-ray imagery data to the OEC 9800 unit 1940 in a format that the OEC 9800 unit 1940 can understand, whereby the OEC 9800 unit 1940 can then process and display that data to a surgeon in an emergency room, for example.

FIG. 22 shows a format 2200 for a second preferred mode in which data is provided to the OEC 9800 unit 1940, whereby the AIMI 1950 converts imagery data obtained from the DFN 1920 into the particular format shown in FIG. 22.

In its current configuration, the DFN 1920 has three test connector input/output ports: a J9-LB connector, a J10-FC connector, and a J11-DAP connector. In the first embodiment, at least two of these connector I/O ports are utilized to communicatively couple the AIMI 1950 with the DFN 1920. Also, in a preferred implementation, the Field Programmable Gate Arrays (FGPAs) used in the DFN 1920 and the AIMI 1950 are FPGAs manufactured by Altera; for example, Altera's APEX20KE EP20K400EFC672 FPGA model may be utilized. However, the firmware used with those FGPAs will be in accordance with the description of the various embodiments of the invention as described herein.

Figure 23:
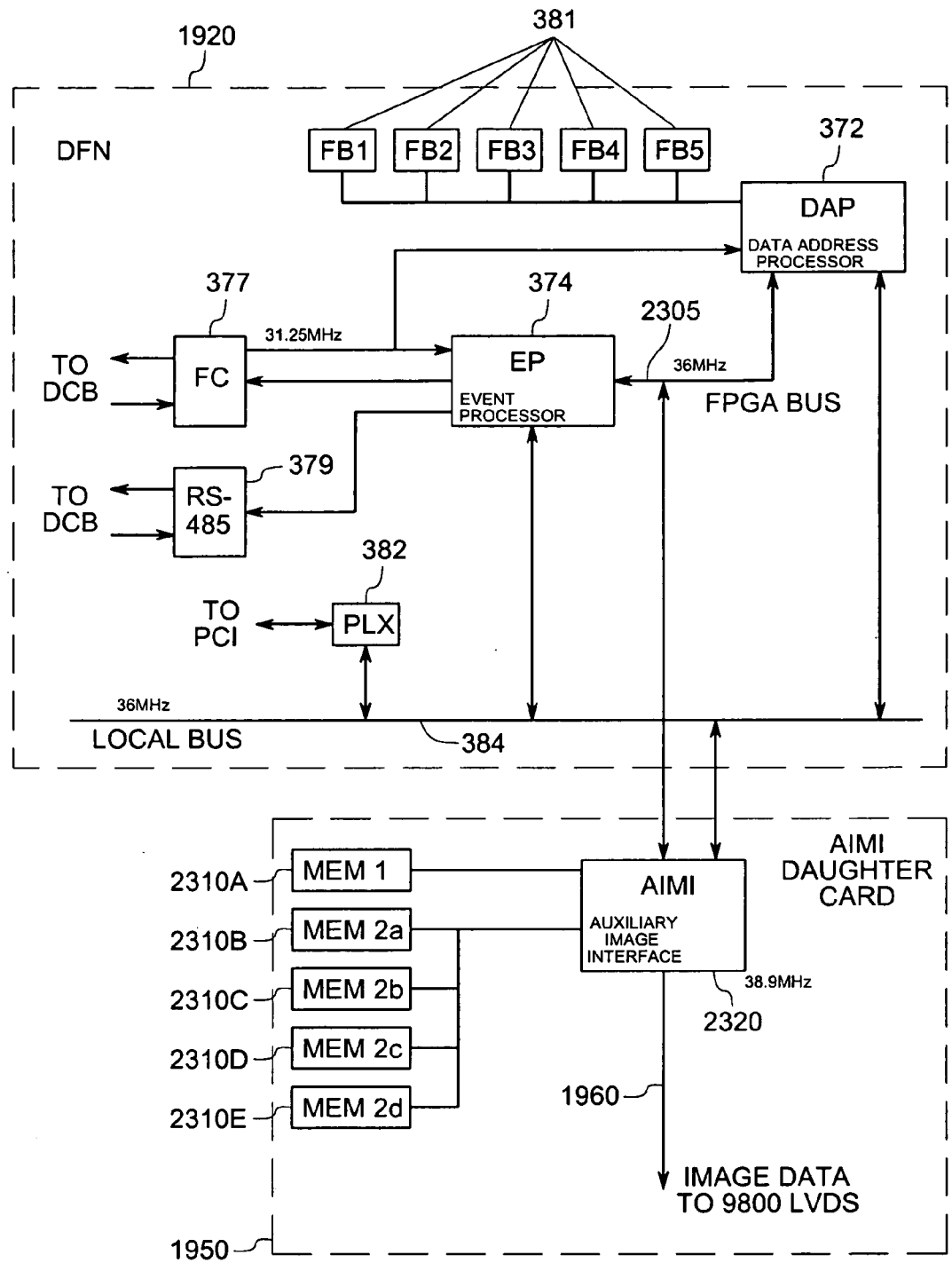
FIG. 23 shows a functional diagram of the AIMI and the DFN, in accordance with a first embodiment of the invention.

FIG. 23 shows a functional diagram of the AIMI 1950 and the DFN 1920, in accordance with a first embodiment of the invention. As shown in FIG. 23, the AIMI 1950 includes five separate memories 2310A–2310E, which are of sufficient size to respectively hold one offset map and four gain maps (to be used to modify the data based on the x-ray intensity values, for example). The AIMI 1950 also includes a FPGA 2320, which is coupled to a Local Bus 384 of the DFN 1920. The AIMI's FGPA 2320 will DMA the image data from the Data Address Processor (DAP) 2330 (of the DFN 1920) over the Local Bus 384, perform any desired processing (e.g., pixel offset and gain processing), and communicate the data to the OEC 9800 unit 1940 via LVDS lines 1960. In a preferred configuration, data is output on the LVDS lines 1960 at a pixel clock of 38.93×106 Hz (see Mode 1 characteristics as shown in FIG. 21). The DAP 372 and the Event Processor 374 are coupled to each other by an FGPA Bus 2305 (as well as by the local bus 384), whereby the FGPA bus 2305 bus is exclusively dedicated to data transfer between these two FGPAs. The DAP 372 manages the frame buffer memories 381 and is notified when any of them are full of data as output by the detector 116. The DAP 372 receives the data from the detector and writes it to memory. Therefore the DAP 372 manages the memory address to write the data to and knows when a memory buffer is full. The detector 116 has no knowledge of what the DFN 372 does with the data and therefore is not in a position to inform the DAP 372 when a memory buffer is full. The DAP 372 notifies the Event Processor 374 when one of the frame buffer memories 381 is full via a signal sent over the private FGPA bus 2305. The Event Processor 374 then issues the DMA command to the PLX 382 over the local bus 384, whereby the DMA command was supplied beforehand (during setup of the DFN 1920) by the DFN Driver.

When the AIMI 1950 is not present in the system, the DMA command includes the origin address, the destination address, the number of bytes to transfer, DMA Enable, DMA Execute, and Notify When Done. When the DMA transfer is complete, the PLX 382 sends an interrupt to the DFN 1920 indicating completion.

In order to perform the data processing necessary to convert data from the DFN 1920 into a format that is readable by the OEC 9800 unit 1940, the AIMI's FGPA 2320 is communicatively coupled to the Local Bus 384 and to the FPGA Bus 374 of the DFN 1920. In a preferred implementation of the first embodiment, the AIMI 1950 receives configuration information by way of PCI addressable registers. In particular, the configuration information is read from the PCI bus (see bus 302 in FIG. 15) by the Computer Communication Interface (also referred to as "PLX unit" or "PLX" in this application) 382 of the DFN 1920, and transferred at the appropriate clock rate to the local bus 384 of the DFN 1920. The AIMI 1950 monitors the local bus 384, and retrieves any addresses and corresponding data that is assigned to its PCI register address range. In a preferred implementation, the local bus 384 is a 36 MHz PCI bus.

Figure 24:
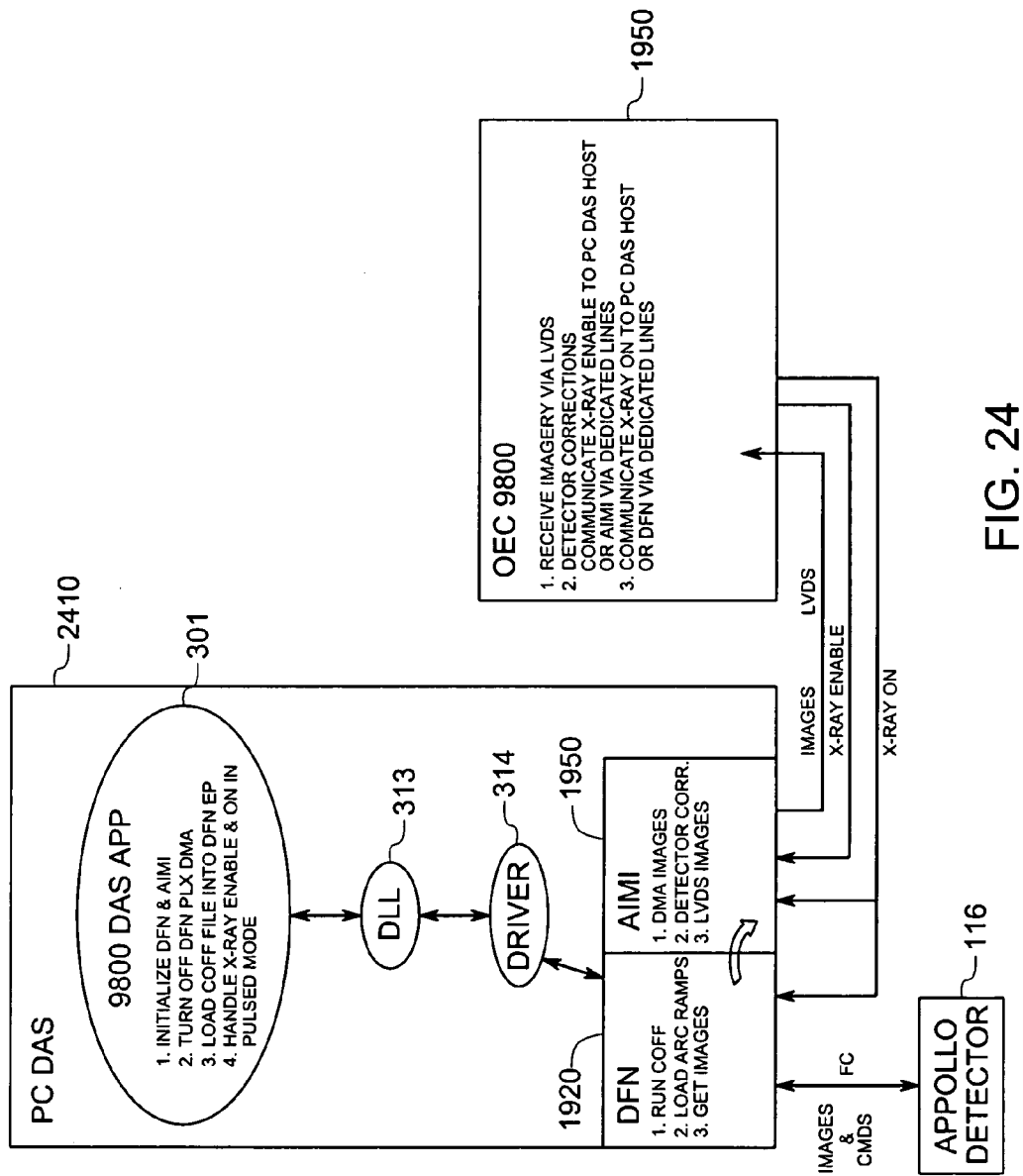
FIG. 24 shows a system configuration of an imaging system according to at least one embodiment of the invention.

When imagery data is provided from the DCB 124 (see FIG. 6) of the Apollo detector 116 to the DFN 1920, by way of the Fiber Channel Interface 2305 shown in FIG. 23, due to a read of the detector 116 by the DFN 1920, the image data is written into one or more of the Frame Buffer Memories 381 of the DFN 1920. In more detail, with reference to FIG. 24, the OEC 9800 unit 1940: a) receives imagery data via LVDS lines 1960 from the AIMI 1950, b)

performs detector corrections as needed, c) communicates an X-RAY_ONX-RAY ENABLE signal to the AIMI 1950 (and/or to the PC DAS host processor 2410 in an alternate embodiment via dedicated control lines, and d) communicates a X-RAY ON signal, as needed, to the PC DAS host processor 2410 via dedicated lines. The PC DAS host processor 2410: a) initiializes the DFN 1920 and the AIMI 1950, b) turns off the DMA start in a DMA command sent to the DFN 1920 (and read by the AIMI 1950) when the AIMI 1950 is provided in the system, c) loads appropriate application programs into the Event Processor 374 of the DFN 1920, and d) handles X-RAY ENABLE and X-RAY ON controls, in pulsed mode. As shown in FIG. 24, the PC DAS host processor 2410 communicates with the DFN 1920 by way of DLL 313 and DFN Device Driver 314 (see also FIG. 15). The DFN 1920: a) runs the application programs as provided by the DAS host processor 2410, b) configures the Apollo detector 116 and c) obtains x-ray images from the Apollo Detector 116. The AIMI 1950: a) performs DMA of x-ray image data stored in the DFN 1920, b) performs any detector correction processing, as required, c) performs format modification of the x-ray image data, and d) outputs the format-modified data over LVDS lines 1960 to the OEC 9800 unit 1940.

The PC DAS host processor 2410 is notified as to whether or not the AIMI 1950 is provided in the system. If it is provided, then x-ray imagery data is not sent to the PC DAS host processor 2410 by way of DMAs to the DFN 1920, but rather the AIMI 1950 performs DMAs of the imagery data stored in the DFN 1920 and reformats it in a different format (see FIG. 21 or FIG. 22) to be output to the OEC 9800 unit 1940.

The AIMI 1950 provides a data path from the Apollo DCB 124, through the DFN 1920, into the AIMI 1950, with the output in a format acceptable to the OEC 9800 unit 1940, via LVDS lines 1960. The AIMI 1950 enables a basic integration testing with a DCB generating a test pattern, for example. Panel size, H Blank, V Blank parameters are set via PCI addressable registers, thereby providing flexibility in simulation and in system integration. Also, pixel offset processing and gain processing can also be provided to the AIMI 1950, by way of PCI addressable registers.

Figure 25:
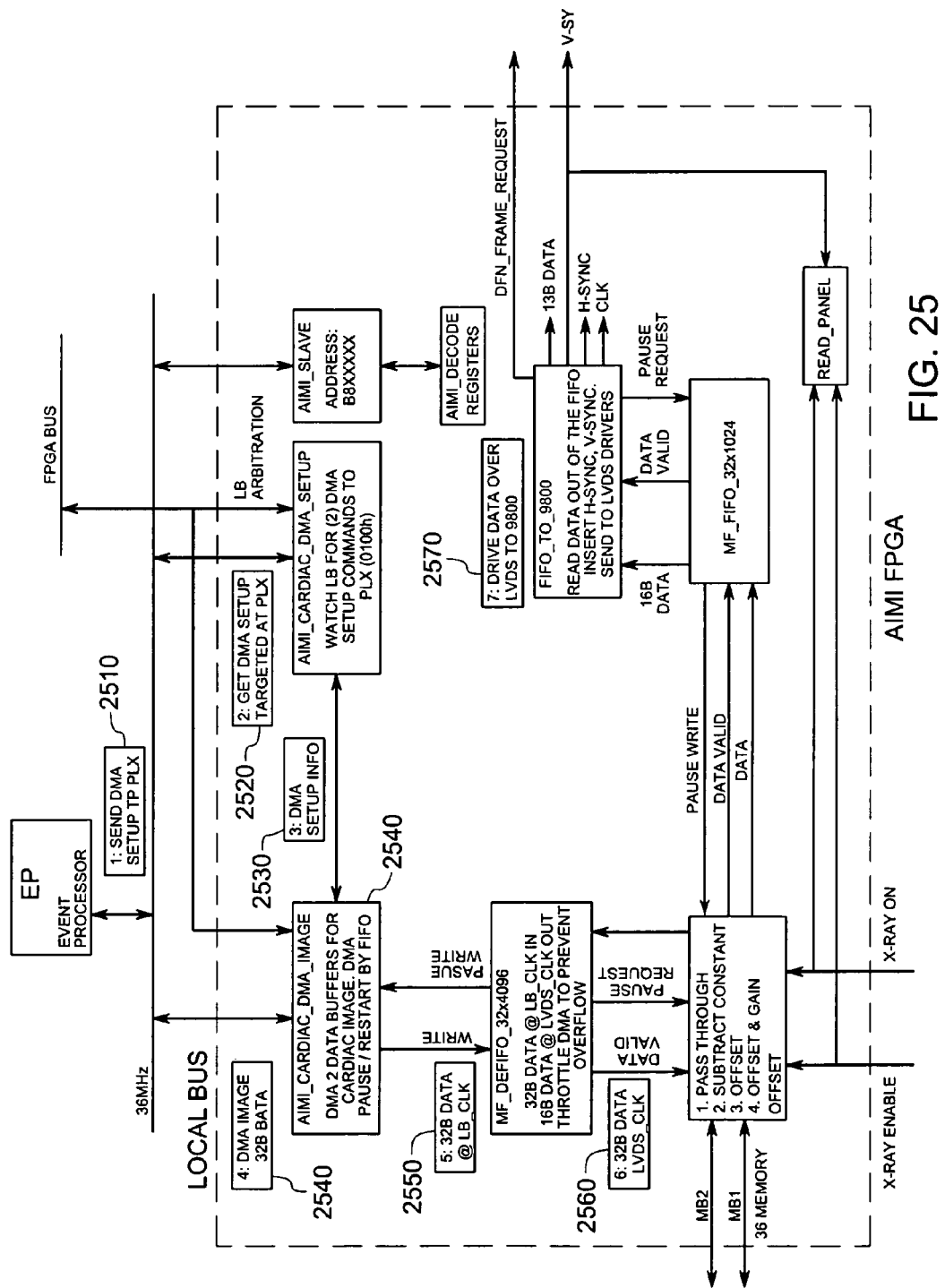
FIG. 25 shows the steps performed by firmware programmed into the various FGPAs of the DFN and the AIMI according to at least one embodiment of the invention.

FIG. 25 shows the steps performed by firmware programmed into the various FGPAs of the DFN 1920 and the AIMI 1950 according to the first embodiment of the invention. In a first mode of operation in which the AIMI 1950 is not provided in the image system, the Event Processor 374 of the DFN 1920 is notified by the DAP 372 that one or more of the frame buffer memories 381 is full with image data, and the Event Processor 374 issues a DMA command to the PLX unit 382 over the local bus 384, whereby the imagery data is output to a memory of the PC DAS host processor 2410 (for display on a display unit, for example) by way of the PLX unit 382 and the local bus 384. In more detail, as the DFN 1920 reads data from the detector 116, the DFN 1920 stores the data in a series of frame buffer memories 381. As each buffer is filled, the DFN 1920 signals that the buffer is full via a DMA command output by the Event Processor 374 to the PLX unit 382 of the DFN 1920. In that way, imagery data is read from the frame buffer memories and sent to the host processor 2410. However, in a second mode of operation in which the AIMI 1950 is provided in the image system, the AIMI 1950 is the device that actually requests a DMA transfer, since the DFN 1920 outputs a dummy DMA command in this instance. The image data transfer operation when the AIMI 1950 is present is similar to the image data transfer operation when the AIMI 1950 is not present, but in this case the DMA command issued by the Event Processor 374 has the DMA Execute and DMA Enable bits unasserted, whereby this results in a 'dummy' DMA command being issued by the Event Processor 374 to the PLX unit 382. The steps performed when the AIMI 1950 is present in the system are described in detail below.

In a first step 2510 as shown in FIG. 25, the Event Processor 374 sends to the PLX 382 (also referred to as the Computer Communication Interface in FIG. 18, which functions to provide an electrical interface to the PCI bus) a DMA command and set up information. In a preferred implementation, the Event Processor's DMACMD register, address A000B8h, is written to the PLX's DMACRSO register for each DMA. The PC DAS Driver 314 writes to the Event Processor's DMACMD register in response to a DLL DFNBeginSequence command, which signifies a time to start retrieving imagery stored the DFN 1920 (as obtained from the Apollo detector's DCB 124). Unlike the first mode of operation in which the AIMI 1950 is not present and whereby the DMA command is a "real" command, in the second mode of operation (in which the AIMI 1950 is present in the system) the DMA command is a "dummy" DMA command, whereby a bit is set in the DMA command to disable the start of a DMA transfer. Thus, the PLX 382 does not perform any DMA transfer to the PC DAS host processor 2410, since the DMA is never started.

In a second step 2520 as shown in FIG. 25, a firmware module called Aimi_cardiac_dma_setup (as performed by the FGPA 2320 of the AIMI 1950) monitors the local bus 384 for DMA commands sent to the PLX (address 0100h). Upon observing the first DMA setup (whereby this DMA setup is a "dummy" DMA setup), the AIMI 1950 latches the DMA parameters in the first DMA setup and sends a LINT (local bus interrupt) which signals DMA completion. At this time, the DMA has not been performed as yet, but the DAP 372 of the DFN 1920 will not reuse the frame buffer memory that is to provide the DMA data until the DMA for each of the two frame buffer memories which constitute a cardiac image has been completed. This is performed so that the AIMI 1950 has the addresses for both halves of the cardiac image at the beginning of the transfer. This ensures that AIMI 1950 does not wait for the addresses fro the second half of the image after acquiring and transmitting the first half of the image to the OEC 9800 unit 1940. Such a delay would violate the AIMI/9800 communications protocol and result in a hardware error. In the present invention, the DFN 1920 performs two DMAs per image for reordered cardiac data. The firmware modules described herein with the word "cardiac" as part of their name make the assumption that there will be two DMAs per image.

Upon observing the LINT, the Event Processor 374 issues the second DMA setup (since there are two DMA's per image for cardiac data) to the PLX 382, which is also latched. The second DMA setup command is also a "dummy" DMA command, which disables the start of a DMA transfer. However, the AIMI 1950 reads the second DMA setup command from the local bus 384, and acquires the corresponding DMA parameters for two of the frame buffer memories 381 of the DFN 1920 in which to read data from (in a DMA transfer). Having acquired the DMA parameters for two frame buffer memories 381, the firmware module aimi_cardiac_dma_setup sends the information to a firmware module (also performed by the FGPA 2320 of the AIMI 1950) called aimi_cardiac_dma_image, along with a control signal asserting that the DMA setup is complete.

In the third through fifth steps 2530, 2540, 2550 as shown in FIG. 25, the AIMI 1950 DMAs the image from the DAP 372 and writes it into a FIFO within the AIMI 1950, for possible data manipulation and eventual transfer to the OEC 9800 unit 1940' via LVDS lines 1960. In particular, DMA setup information is sent from the aimi_cardiac_dma_setup module to the aimi_cardiac_dma_image module. The aimi_cardiac_image module of the AIMI 1950 latches the DMA parameters from the aimi_cardiac_dma_setup module of the AIMI 1950, upon assertion of DMA setup complete (which is output at the end of step 2, as described above). It then arbitrates for the local bus 384, and begins the DMA of the first buffer of the frame buffer memory units 381 of the DFN 1920 (under read/write control by the DAP 372). The data is output to a FIFO, shown as mf_dcfifo__32__4096 module in FIG. 25, as it is received. The "mf_" prefix is used here to denote an Altera Quartz mega-function, and "dc" denotes dual clock, as is utilized in a preferred construction of the first embodiment. "Mega" functions use "ESB" resources as opposed to device logic on the FGPA.

The DMA_FIFO_PAUSE process tracks FIFO usage, and will request writes to the FIFO to be paused to prevent FIFO overflows. When a pause is requested, the DMA is stopped, and the local bus 384 is released by the AIMI 1950 until the FIFO write pause is cleared. Such a clearance may be by monitoring the current amount of data held in the FIFO, whereby if the current amount of data is at least a certain amount (e.g., 50% full) below the maximum storage capacity of the FIFO, the FIFO write pause is cleared. As is the case with most types of DMAs, the data is being written into the FIFO at a faster rate than the data is being read out of the FIFO (on its way to the OEC 9800 unit 1940). When the FIFO write pause is cleared, then the aimi_cardiac_dma_image module arbitrates for the local bus 384, and when it obtains control of the local bus 384 it continues the DMA where it had left off.

The DMA of the second frame buffer memory of the frame buffer memory units 381 of the DFN 1940 immediately follows completion of the first DMA. On completion of the DMA of the second frame buffer memory, a LINT is output onto the local bus 384 by the AIMI 1950, signaling completion of the DMA transfer. Since this is the second LINT (the first was sent by aimi_cardiac_dma_setup), the DAP 372 of the DFN 1940 assumes that the entire image has been transferred, and releases the frame buffer memory units 381 for reuse (in order to read in new image data from the Apollo detector 116, as provided to the DFN 1940 by way of the DCB 124). In a preferred implementation, the source addresses for the first and second DMAs are the same from image to image. This is due to memory mapping being performed by the DAP 372.

In a sixth step 2560 as shown in FIG. 25, data is loaded onto the FIFO mf_dcfifo__32__4096, which is a dual clock FIFO (within the AIMI 1950) with different input and output clock rates. The output of the FIFO is 32 bits at the LVDS clock rate, so as to be clock compatible with subsequent processing and to compatible to the clock rate at which data is received by the OEC 9800 unit 1940. The FIFO mf_dcfifo__32__4096 provides data to an offset module, which is capable of performing one of the following processes: a) pass through without modifying the data, b) subtract a constant to the data prior to outputting the data, c) provide an offset to the data prior to outputting the data, and d) providing an offset and a gain to the data prior to outputting the data. As shown in FIG. 25, the offset module receives two separate control signals, X-RAY_ENABLE and X-RAY_ON, which signify when the Apollo detector flat panel 116 is currently receiving imaging signals output from an imaging generator (see FIG. 1, for example). Based on these signals, the timing of reads and writes used to provide the appropriate gain and/or offset manipulation of the imagery data, is coordinated with receipt of real imagery data.

As shown in the sixth step 2560 in FIG. 25, the offset module is provided between the FIFO mc_dc__32 256, and the FIFO mf_fifo__32×1024. One purpose of the subtracting of a constant from the detector flat panel's image data is to reduce the offset to be within the dynamic range of the OEC 9800 unit 1940. Also, in the times when a constant illumination signal is provided directly to the Apollo detector flat panel 116, based on the pixel signal level of each pixel of the Apollo detector flat panel 116, offset processing may need to be performed in order to account for any variations among the pixels due to manufacturing irregularities of components (e.g., transistors) of the Apollo detector flat panel 116. These irregularities are corrected by way of the offset module, whereby the operation of the offset module will be described in more detail in a later section.

Like the other modules, the offset module is configured via PCI addressable registers, whereby it can be controlled to perform a desired amount of pixel offset and/or gain control by way of a host processor.

Similar to the DMA FIFO, the AIMI module LVDS_FIFO_PAUSE tracks the usage of the FIFO mf_fifo__32×128, and requests the offset module to suspend writing when the FIFO mf_fifo__32×128 is approaching its maximum storage capacity. The pause signal is de-asserted when the FIFO mf_fifo__32×1024 drops below 50% full.

In a seventh step 2570 as shown in FIG. 25, data is read from the FIFO, formatted with synchronization and blanking signals, and output over LVDS signaling lines 1960 to the OEC 9800 unit 1940. In particular, module FIFO_to__9800 draws two pixels at a time from the fifo mf_fifo__32×1024 as needed, and formats it for the OEC 9800 unit 1940. Specifically, in a preferred implementation of the first embodiment, the two most significant bits (MSBs) of the data are omitted, and H-blank and V-blank are inserted. Image size, V-blank and H-blank are specified in parameter registers, as obtained by the AIMI 1950 by way of module AIMI_Slave 2560 and the module AIMI_Decode 2570 (which decodes the information received by AIMI_Slave module 2560). AIMI_Slave module 2570 monitors the local bus 384 of the DFN 1920 for any PCI addresses that are within the range of the AIM 1950, and if so, it reads the addresses and the corresponding data, which is in turn decoded by the AIMI_Decode module 2570.

In preparing the data for output onto the LVDS lines 1960 (to be read off of those lines by the OEC 9800 unit 1940), in a preferred implementation, te firmware must consider the synchronization of x-ray pulses from the 9800 and reading the Apollo panel, performed by the DFN 1920. The OEC 9800 unit 1940 uses V-Sync for synchronizing x-ray pulses. The DFN 1920 uses DFN_Read_Request for the timing of when to read the Apollo panel.

Figure 26:
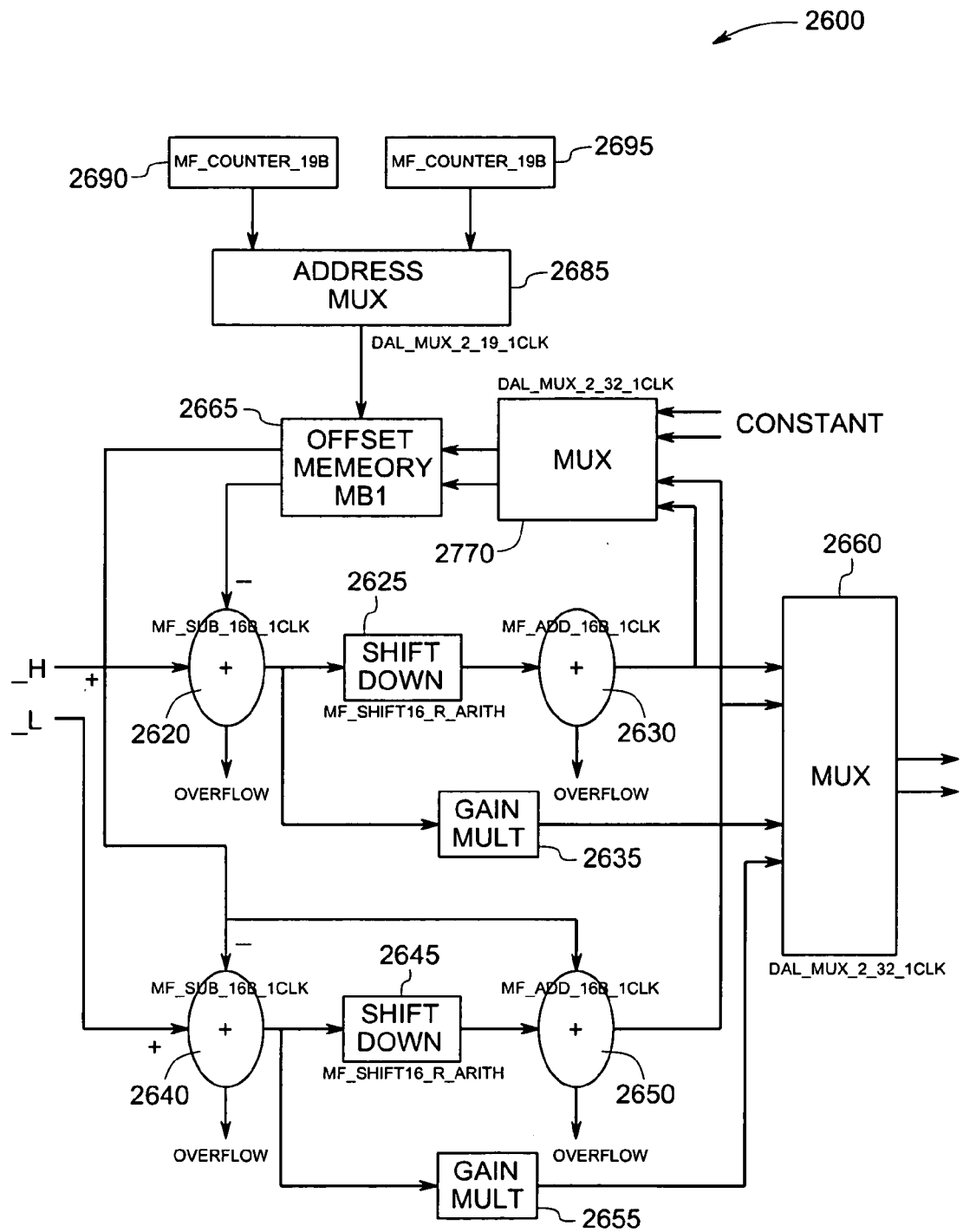
FIG. 26 shows the offset processing architecture 2600 that is utilized by the offset module of the AIMI, according to a second embodiment of the invention.

The communication protocol from AIMI 1950 to the OEC 9800 unit 1940 is based of 30 FPS image communication regardless of the X-Ray pulse FPS (frames per second). The firmware module Read_Panel has knowledge of the desired X-ray FPS from the AIMI register space. It coordinates reading of the panel with X-Ray pulses and additionally ensures the panel is synchronously read when x-rays are not being generated. This is important to proper operation of the Apollo detector 116 which requires it be read synchronously. The images read from the Apollo digital detector require offset and gain data corrections. The offset and gain vary for each pixel. The offset slowly varies over time and must be monitored when the detector is not being illuminated with x-rays. The gain is static and only needs to be estimated once. The AIMI 1950 may optionally perform offset and gain corrections. Additionally, the AIMI 1950 supports a constant offset and gain value providing partial detector correction with final corrections performed in downstream processing in the OEC 9800 unit 1940. A second embodiment of the invention will be described below, with reference to the computations performed by the offset module of the AIMI 1950. In the second embodiment, the offset processing is performed such that reads and writes are sequentially performed in consecutive clock cycles by the offset module. FIG. 26 shows the offset processing architecture 2600 that is utilized by the offset module of the AIMI 1950, in order to perform offset and/or gain processing on the received image data, prior to outputting that data to the OEC 9800 unit 1940.

In a preferred implementation of the second embodiment, each pixel corresponds to 16 bits of data, and data is received by the offset module as 32 bit words, thereby corresponding to data from two adjacent pixels of the flat panel display 16. Each 16-bit pixel is handled in a separate data path, and represented in FIG. 26 by either an "_H" for the highest 16 bits of the 32 bit word received by the offset module, or "_L" for the lowest 16 bits of the 32 bit word received by the offset module. The structure shown in FIG. 26 processes both pixels at the same time, on two separate paths. While such a structure requires more elements, specifically two adders and a shifter, it is a preferred construction since only a small portion of the FGPA 2320 of the AIMI 1950 is utilized in the present invention, thereby allowing for such use of additional portions of the FGPA 2320 at a minor resource usage expense while at the same time allowing for a simpler and faster data flow.

With the structure shown in FIG. 26, through multiplexer settings and memory enable, the offset module can be configured for unity transform (no manipulation of the input data), for subtracting a constant, and/or for calculating an offset mask and for performing offset correction. Shift amount, subtraction constant, and x-ray ON information are established via PCI addressable registers, in a preferred implementation of the second embodiment.

The offset module architecture shown in FIG. 26 includes a first adder 2620, a first shifter 2625, a second adder 2630, and a first gain multiplier 2635 provided on the "_H" pixel path. Also, a third adder 2640, a second shifter 2645, a fourth adder 2650, and a second gain multiplier 2655 are provided on the "_L" pixel path. Outputs from these two paths are provided to a first multiplexer (MUX) 2660, which provides output data to module mf_fifo_32×128 as seen in FIG. 25.

Referring back to FIG. 26, an offset memory 2665 is provided in the offset module architecture 2600, whereby the offset memory 2665 receives feedback data from the first and second paths or which receives "constant" data, in accordance with a setting of a second MUX 2670. The "constant" data may be provided directly from the OEC 9800 unit 1940, for example, to correct the imagery data so that it can be received and properly displayed on a display unit of the OEC 9800 unit 1940.

The feedback paths to the offset memory 2665 provide a feedback value of the most recent offset value to be provided for a corresponding pixel location of the Apollo flat panel display 116, whereby the corresponding pixel offset value is subtracted from the input pixel value (either _H pixel or _L pixel, depending on the path). Referring now to the _H path, whereby a similar arrangement is provided for the _L path, the subtraction result of the first adder 2620 is shifted down a particular amount, for example, by 4 bit shifts, to provide a value corresponding to 1/16th of the output of the first adder 2620. The bit-shifted value is then added to the pixel offset value output by the offset memory 2625, and the addition result is fed to one port of the second MUX 2670. When the offset module is operating automatically (without offset control as provided by the OEC 9800 unit 1940), the fed back value is used to create a new pixel offset value to be written into the offset memory 2665 for the corresponding pixel location for the next image output from the flat panel display 116. (this corresponds to a first order temporal infinite impulse response (IIR) filter y (i)=y(i−1)+s☆(x−y (i−1)).)

FIG. 26 also shows a read address control counter 2690 and a write address control counter 2695, which provides respective outputs to a third MUX 2685, to thereby retrieve the appropriate pixel offset value from the offset memory 2665, or to write the appropriate updated pixel offset value to the offset memory 2665. As explained above, a read process (with respect to the offset memory 2665) is performed in one clock cycle, and a write process (with respect to the offset memory 2665) is performed in the next clock cycle, a read process is performed in the next clock cycle, a write process is performed in the next clock cycle, and so forth. This interleaving of read and write cycles does not pose a problem with respect to meeting the output data rate, since the DMA data is provided to the AIMI 1950 at a faster rate than the data is being output over the LVDS lines 1960 to the OEC 9800 unit 1940.

Also, with this structure, when no imagery data is being received by the flat panel detector 116, and hence no imagery data is being received by the AIMI 1950, the offset module is configured to output "zeros" in a proper format (see formats in FIG. 21 or FIG. 22, for example) over the LVDS lines 1960 to the OEC 9800 unit 1940. This is because the OEC 9800 unit 1940 receives data no matter whether or not any imaging is currently being performed, whereby the "zero" data is processed by the OEC 9800 unit 1940 as a "blank" (e.g., white) display.

As explained above, when the AIMI 1950 is to perform offset image correction, it needs to know when the flat panel detector 116 is exposed to x-rays. When the flat panel detector 116 is exposed to x-rays, an offset map is applied to the exposed data. In a preferred implementation, a double buffer is used for panel readout pixel reordering, and thereby a one-frame latency occurs prior to the point in the processing chain where the offset image correction processing would occur. As such, the AIMI 1950 requires to be informed about the x-ray exposure with no less than a one frame of latency. Toward that end, an external signal, X-RAY_ON, is generated by the OEC 9800 unit 1940, and is received by the AIMI 1950 to determine when x-ray exposure has occurred. In a preferred construction, the AIMI 1950 has a PCI addressable register that is interpreted as the external signal X-RAY_ON.

In an alternative construction of the second embodiment, the AIMI 1950 determines whether or not a frame was exposed automatically. After DMA setup but before the DMA data transfer begins, the entire frame is available in the frame buffer memory units 381 of the DFN 1920. In this alternative construction of the second embodiment, a small central portion of the image data is read, averaged, and compared to a threshold to determine if it corresponds to x-ray-exposed data. The threshold is a function of the ARC ramp, and is updated with ARC ramp changes.

In a third embodiment of the invention, X-ray pulses are synchronized between reads of the flat panel display 116. For a pulsed (e.g., CINE) x-ray mode of operation, it is possible to synchronize the x-ray pulses to occur between reads of the flat panel display 116. For example, reading a 20 cm Apollo panel requires 21 msec with the remaining time (12 ms for 30 FPS) available for the X-ray pulse.

In the third embodiment, the x-ray pulses output by the x-ray generator are started relative to the Vertical sync pulse which is produced by the AIMI 1950. X-rays start in Fluoro or continuous modes from the leading edge (the beginning) of the Vertical sync. In CINE pulse mode, the pulse is from 3 msec to 10 msec in duration, and will start on the leading edge of the Vertical sync. X-rays will begin at 7 usec+/−3 usec from this edge.

In the first through third embodiments, the PC DAS application residing on the AIMI host processor communicates ARC ramp changes to the DFN 1920, by way of the AIMI 1950. Values in the Offset Memory (see FIG. 26) may be reset based on a change in ARC ramps. In this regard, the PC DAS application will send an Offset_Reset signal to the AIMI 1950. The AIMI 1950 is capable of storing four different gain maps (see memories 2310B–2310E in FIG. 23), to account for different ARC Ramps are utilized.

In a fourth embodiment of the invention, 90 degree rotation of an x-ray image is performed by the DAP 372 of the DFN 1920 reordering the data it receives and writing the reordered data to the frame buffer memory units 381. Address generation logic (to implement the 90 degree rotation) is incorporated into the DAP 372 to accomplish this task. The 90 degree rotation of the image data provides for a pseudo heads-up display of the image data at the 9800 OEC unit 1940, upon operator command.

With respect to each of the embodiments described above, the PC DAS host processor 2410 performs several important functions. The PC DAS host processor 2410 hosts the 9800 host applications, as seen in FIG. 24, whereby those applications are responsible for basic initialization and control. At start-up, the 9800 DAS application opens a COM session with the DFN DLL, and initializes the DFN 1920 and the AIMI 1950 (via PCI addressable registers). Having opened a COM session with the DFN DLL and having initialized the hardware, the 9800 DAS Application loads a COEF file into the DFN 1920. A COEF file is a binary executable file for the DFN's Event Processor 372. The COEF file will: a) initialize the detector flat panel 116, b) read output from the detector flat panel 116 at 30 FPS, and, if desired, c) provide real-time control over the ARC LUTs, frame rate, and detector parameters through use of queue variables and/or RS-485 lines. Queue variables are set via PCI writes, whereas RS-485 inputs represent a dedicated cable between the AIMI 1950 and the DFN 1920.

The use of queue variables for control means that the OEC 9800 unit 1940 will communicate control information to the 9800 DAS Application via serial or some other link. Similarly, the AIMI 1950 requires control signaling for offset and gain detector corrections, as well as for frame rate. As with the DFN 1920, the control signaling may be performed via dedicated wires (e.g., via the LVDS signal lines 1960 from the OEC 9800 unit 1940 to the AIMI 1950), or via PCI writes by way of the 9800 DAS Application. For the AIMI 1950 to perform offset correction, it is provided with the X-RAY_ON signal, which indicates when the x-ray generator is outputting x-rays. For the AIMI 1950 to perform gain correction, it is provided with the Ramp_Sel PCI register, which indicates an output power level of the x-rays. Frame rate changes are also communicated to the AIMI 1950 to the extent that they impact vertical blank and horizontal blank parameters.

Figure 27:
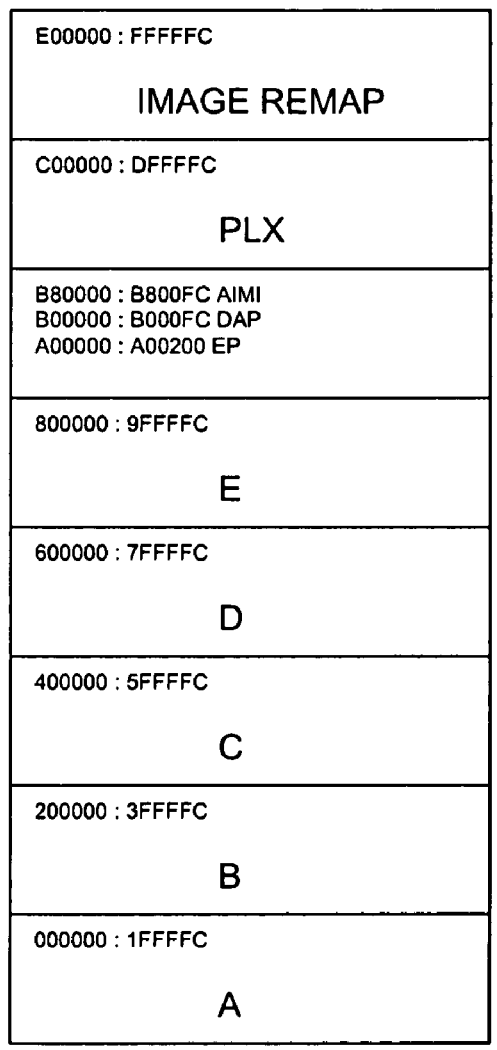
FIG. 27 shows one possible implementation of a memory map for the DFN and for the AIMI, according to at least one embodiment of the invention.

FIG. 27 shows one possible implementation of a memory map 2710 for the DFN 1920 and for the AIMI 1950. In FIG. 27, PCI register addresses E00000 to FFFFC are assigned to Image Remap, PCI register addresses C00000 to DFFFC are assigned to the PLX of the DFN 1920, PCI register addresses B80000 to B800FC are assigned to the AIMI 1950, PCI register addresses B00000 to B000FC are assigned to the DAP 372 of the DFN 1920, PCI register addresses A00000 to A00200 are assigned to the Event Processor 374 of the DFN 1920, and PCI register addresses 000000 to 9FFFFC are respectively assigned to the five frame buffer memory units 381 of the DFN 1920.

In a preferred implementation of the first through fourth embodiments, the AIMI 1950 is provided with a set of 32, 32 bit, PCI addressable registers. These registers are used for configuration, control communications, and status reporting. The first 12 registers are "Status" registers which are set by the AIMI 1950 and are read-only by the local bus 384. For example, the current status of the FIFOs within the AIMI 1950 can be stored in one or more of the Status registers. The next four registers are "Error" registers which are set by the AIMI 1950, any which may only be cleared by the local bus 384. For example, a "FIFO Empty" error message may be stored in one of the Error registers when there is no data in the mf_fifo_32×128 FIFO to be output to the LVDS lines 1960. The last 16 registers are Parameter registers and are read/write by both the AIMI 1950 and the local bus 384. Parameters such as "V_Sync", "H_Sync", "Back Porch and Front Porch size for H_Blank", "Back Porch and Front Porch size for V_Blank", "Line_Period", "DMA Address Register 0", "DMA Address Register 1", and "Offset Parameter", are obtained by the AIMI 1950 from the local bus 384 and stored in a corresponding one of the 16 Parameter registers.

As this invention may be embodied in several forms without departing from the spirit or principal characteristics thereof, the present embodiments are therefore illustrative and not restrictive. Those skilled in the art will appreciate that changes may be made to these embodiments without departing from the principles and spirit of the invention. Accordingly, the scope of the invention is defined by the appended claims rather than by the description preceding them, and all changes that fall within the metes and bounds of the claims, or equivalents of such metes and bounds thereof, are therefore intended to be embraced by the claims. For example, while the present invention has been described with respect to an interface unit for providing data in a proper format for an OEC 9800 unit, it can be applied to any other type of data format to suit another type of device that is configured to receive and process image data. Also, while the AIMI DMA retrieval process has been described with respect to cardiac data, with two DMAs per image, it can also be applied to non-cardiac data whereby only one DMA per image is required.

What is claimed is:

1. An image data acquisition system, comprising:
a detector framing node (DFN) being programmable to receive image data from a panel detector, and to store the image data in at least one buffer for later transfer of the image data by way of a direct memory access (DMA) transfer;
a control unit configured to determine when the at least one buffer is full with the received image data and to output a DMA instruction as a result, the DMA instruction corresponding to a dummy DMA instruction that disables a start of a DMA transfer corresponding to execution of the DMA instruction; and an auxiliary image interface being programmable to detect the dummy DMA instruction, to issue a DMA request to the DFN in accordance with information obtained from the dummy DMA instruction, and to convert data received from the at least one buffer of the DFN into a different format, to output to a host unit that is capable of processing the data received in the different format.

2. The image data acquisition system according to claim 1, wherein the dummy DMA instruction is only output by the control unit when the DMA control unit is notified of an existence of the auxiliary image interface, and wherein the control unit outputs a real DMA instruction to cause the transfer of the image data to a device on a PCI bus when it is determined that the auxiliary image interface is not present in the image data acquisition system.

3. The image data acquisition system according to claim 1, wherein the host unit is an OEC 9800 imaging system.

4. The image data acquisition system according to claim 1, wherein the panel detector is a flat panel detector that outputs digital data.

5. The image data acquisition system according to claim 4, wherein the flat panel detector is an Apollo detector.

6. The image data acquisition system according to claim 1, wherein the different format includes data output with horizontal blanking signals and vertical blanking signals.

7. The image data acquisition system according to claim 6, wherein the different format includes data output with horizontal synchronization signals and vertical synchronization signals.

8. The image data acquisition system according to claim 1, wherein the DFN includes at least one field programmable gate array.

9. The image data acquisition system according to claim 8, wherein the auxiliary image interface includes at least one field programmable gate array and at least one memory for storing at least one of pixel offset values and pixel gain values.

10. The image data acquisition system according to claim 1, further comprising:

a plurality of low voltage differential signal lines provided between the auxiliary image interface and the host unit, wherein data is sent to the host unit by way of the plurality of LVDS lines.

11. The image data acquisition system according to claim 1, wherein the image data received from the panel detector corresponds to x-ray image data.

12. The image data acquisition system according to claim 1, wherein the DFN comprises:

an Event Processor configured to control operation of the panel detector and a radiation system that provides signals to be received by the panel detector;

a plurality of frame buffer memories configured to temporarily store image data output from the panel detector;

a Data Address Processor configured to provide read/write control for the plurality of frame buffer memories;

a Communications Bus Interface unit configured to provide an interface to an external bus by which the DFN communicates with the device on the PCI bus; and a local bus provided for transferring of information between the Event Processor, the Data Address Processor, and the Communications Bus Interface Unit, which are all communicatively coupled to the local bus.

13. An image data acquisition system according to claim 12, wherein the auxiliary interface unit is also communicatively coupled to the local bus, wherein the auxiliary interface unit performs DMA by way of the local bus, the Data Address Processor, and the plurality of frame buffer memories.

14. An image data acquisition system, comprising:

detector framing node (DFN) means for receiving image data from a panel detector, and for storing the image data for later transfer of the image data by way of a direct memory access (DMA) transfer;

control means for controlling operation of the DFN means and for outputting at least one DMA instruction, the at least one DMA instruction corresponding to a dummy DMA instruction that disables a start of a DMA transfer corresponding to execution of the at least one DMA instruction; and auxiliary image interface means for detecting the dummy DMA instruction, for issuing a DMA request to the DFN means in accordance with the dummy DMA instruction, and for converting data received from the DFN means into a different format, to output to a host unit that is capable of processing the data received in the different format.

15. The image data acquisition system according to claim 14, wherein the dummy DMA instruction is only output by the control means when the DMA control unit is notified of an existence of the auxiliary image interface means, and wherein the control means outputs a real DMA instruction to the DFN means to cause the DFN means to transfer data to the DFN control means when the control means determines that the auxiliary image interface is not present in the image data acquisition system.

16. The image data acquisition system according to claim 14, wherein the host unit is an OEC 9800 imaging system.

17. The image data acquisition system according to claim 14, wherein the panel detector is a flat panel detector that outputs digital data.

18. The image data acquisition system according to claim 17, wherein the flat panel detector is an Apollo detector.

19. The image data acquisition system according to claim 14, wherein the different format includes data output with horizontal blanking signals and vertical blanking signals.

20. The image data acquisition system according to claim 19, wherein the different format includes data output with horizontal synchronization signals and vertical synchronization signals.

21. The image data acquisition system according to claim 14, wherein the DFN means includes at least one field programmable gate array.

22. The image data acquisition system according to claim 21, wherein the auxiliary image interface means includes at least one field programmable gate array and at least one memory for storing at least one of pixel offset values and pixel gain values.

23. The image data acquisition system according to claim 14, further comprising:

a plurality of low voltage differential signal lines provided between the auxiliary image interface means and the host unit, wherein data is sent to the host unit from the auxiliary image interface means by way of the plurality of LVDS lines.

24. The image data acquisition system according to claim 14, wherein the image data received from the panel detector corresponds to x-ray image data.

25. The image data acquisition system according to claim 14, wherein the DFN means comprises:

an Event Processor configured to control operation of the panel detector and a radiation system that provides signals to be received by the panel detector;

a plurality of frame buffer memories configured to temporarily store image data output from the panel detector;

a Data Address Processor configured to provide read/write control for the plurality of frame buffer memories;

a Communications Bus Interface unit configured to provide an interface to an external bus by which the DFN means communicates with the DFN control means; and a local bus provided for transferring of information between the Event Processor, the Data Address Processor, and the Communications Bus Interface Unit, which are all communicatively coupled to the local bus.

26. An image data acquisition system according to claim 25, wherein the auxiliary interface unit is also communicatively coupled to the local bus, wherein the auxiliary interface unit performs DMA by way of the local bus, the Data Address Processor, and the plurality of frame buffer memories.

27. An image data acquisition method, comprising:

receiving image data at a detector framing node as output from a panel detector, and storing the image data for later transfer of the image data by way of a direct memory access (DMA) transfer;

controlling operation of the DFN and outputting at least one DMA instruction to the DFN, the at least one DMA instruction corresponding to a dummy DMA instruction that disables a start of a DMA transfer corresponding to execution of the at least one DMA instruction;

detecting, by way of an auxiliary image interface means unit communicatively coupled to the DFN, the dummy DMA instruction, for issuing a DMA request to the DFN in accordance with the dummy DMA instruction;

converting data received from the DFN into a different format; and outputting the converted data to a host unit that is capable of processing the data received in the different format.

28. The image data acquisition method according to claim 27, wherein the dummy DMA instruction is only output when the auxiliary image interface is determined to be present, and wherein a real DMA instruction is output to cause the DFN to transfer data to a unit other than the host unit when it is determined that the auxiliary image interface is not present.

29. The image data acquisition method according to claim 27, wherein the host unit is an OEC 9800 imaging system.

30. The image data acquisition method according to claim 27, wherein the panel detector is a flat panel detector that outputs digital data.

31. The image data acquisition method according to claim 30, wherein the flat panel detector is an Apollo detector.

32. The image data acquisition method according to claim 27, wherein the different format includes data output with horizontal blanking signals and vertical blanking signals.

33. The image data acquisition method according to claim 32, wherein the different format includes data output with horizontal synchronization signals and vertical synchronization signals.

34. The image data acquisition method according to claim 27, wherein the DFN includes at least one field programmable gate array.

35. The image data acquisition method according to claim 34, wherein the auxiliary image interface includes at least one field programmable gate array.

* * * * *